United States Patent [19]

Nelson et al.

[11] Patent Number: 5,169,944
[45] Date of Patent: Dec. 8, 1992

[54] METHODS AND COMPOSITIONS FOR THE ENTERAL ADMINISTRATION OF HEPATOBILIARY MRI CONTRAST AGENTS

[75] Inventors: James A. Nelson, Seattle; Udo P. Schmiedl, Kirkland; Linnar L. Teng, Bothell, all of Wash.; Jerry C. Bommer, Wellsville, Utah

[73] Assignee: Board of Regents of the University of Washington, Seattle, Wash.

[21] Appl. No.: 685,083

[22] Filed: Apr. 12, 1991

[51] Int. Cl.$^5$ .................. A61B 5/055; C07D 487/22; G01N 24/08

[52] U.S. Cl. ................................. 540/145; 128/653.4

[58] Field of Search ............... 540/145; 514/185, 410, 514/427; 436/173; 424/9; 128/653 CA

[56] References Cited

U.S. PATENT DOCUMENTS

| | | | |
|---|---|---|---|
| 4,393,071 | 7/1983 | Fujii et al. | 424/274 |
| 4,656,186 | 4/1987 | Bommer | 514/410 |
| 4,797,392 | 1/1989 | Chernomorsky | 514/185 |
| 4,804,529 | 2/1989 | Bardy et al. | 424/9 |
| 4,877,872 | 10/1989 | Morgan et al. | 540/145 |
| 4,899,755 | 2/1990 | Lauffer et al. | 128/654 |
| 5,051,415 | 9/1991 | Morgan et al. | 514/185 |
| 5,053,423 | 10/1991 | Liu | 514/410 |

OTHER PUBLICATIONS

Fawwaz, R. et al., "Use of Metalloporphyrins in Diagnostic Imaging," *Nucl. Med. Biol.* 17(1):65-72, 1990.

Fiel, R. J. et al., "A Comparative Study of Manganese meso-Sulfonatophenyl Porphyrins: Contrast-Enhancing Agents for Tumors," *Magnetic Resonance Imaging* 8:255-259, 1990.

Jackson, L. S. et al., "Manganese Protoporphyrin IX; A Potential Intravenous Paramagnetic NMR Contrast Agent: Preliminary Communication," *Investigative Radiology,* Mar.-Apr. 1985, vol. 20, No. 2, J. B. Lippincott Co. publishers, pp. 226-229.

Nelson, J. A. et al., "Kinetic Studies of Manganese Mesoporphyrin," *Contrast Agents in MR Imaging,* 1986, Range, Claussen, Felix, James editors, pp. 74-75.

Cegnar, J. M. et al., "Adsorption of Lipophilic Contrast Agent with Cholestyramine," poster presentation, Association of University Radiologists, 1987.

Place, D. A. et al., "Metalloporphyrins as Contrast Agents for Tumors in MRI," abstract M24 from meeting of Oct. 8-13, 1989 of Contrast Media Research held at Sydney and Hamilton Island, Australia.

Nelson, J. A. et al., "Metalloporphyrins as Tumor Seeking MRI Contrast Media and as Potential Selective Treatment Sensitizers," abstract from meeting of Oct. 8-13, 1989 of Contrast Media Research held at Sydney and Hamilton Island, Australia.

Nelson, J. A. et al., "Metalloporphyrins as Tumor Seeking MRI Contrast Media as Potential Selective Treatment Sensitizers," *Invest. Radiol* 25:571-573, 1990.

Rose, I. S. et al., "Effect of Ingestion of Hemoproteins on Fecal Excretion of Hemes and Porphyrins," *Clinical Chemistry* 35(12):2290-2296, 1989.

Bohdiewicz, P. J. et al., "Mn (III) Hematoporphyrin: A Potential MR Contrast Agent," *Investigative Radiology* 25:765-797, 1990.

Cory, D. A. et al., "Ingested Manganese Chloride as a Contrast Agent for Magnetic Resonance Imaging," *Magnetic Resonance Imaging* 1986.

(List continued on next page.)

*Primary Examiner*—Marianne M. Cintins
*Assistant Examiner*—Michael B. Hydorn
*Attorney, Agent, or Firm*—Christensen, O'Connor, Johnson & Kindness

[57] ABSTRACT

Hepatobiliary magnetic resonance imaging of a human or animal subject is enhanced by enterally administering to the subject an effective amount of a lipophilic contrast enhancing agent. Representative contrast enhancing agents include manganese mesoporphyrin, manganese deuteroporphyrin, manganese pheophorbide and manganese pyrophenophoribide, and, when administered orally, an enteric delivery agent.

14 Claims, 7 Drawing Sheets

OTHER PUBLICATIONS

Vreman, H. J. et al., "Effects of Oral Administration of Tin and Zinc Protoporphyrin on Neonatal and Adult Rat Tissue Heme Oxygenase Activity," *Journal of Pediatric Gastroenterology and Nutrition* 7:902-906, 1988.

Unger, E. C. et al., "Hepatic Metastases: Lipsomal Gd-DTPA-enhanced MR Imaging," *Radiology* 171:81-85, 1989.

Young, S. W. et al., "Detection of Hepatic Malignancies Using Mn-DPDP (Manganese Dipyridoxal Diphosphate) Hepatobiliary MRI Contrast Agent," *Magnetic Resonance Imaging* 8:267-276, 1990.

Anderson, K. E. et al., "Disposition of tin-protoporphyrin and Suppression of Hyperbilirubinemia in Humans," *Clin. Pharmacol. Ther.* 39(5):510-519, 1985.

Iwai, K. et al., "Tumor Uptake of [$^{48}$V]Vanadyl-Chlorine e$_6$Na as a Tumor-imaging Agent in Tumor-bearing Mice," *Nucl. Med. Biol.* 178(8):775-780, 1990.

Nelson, J. A. et al., "Manganese Mesoporphyrin: Hepatobiliary MRI Contrast Characteristics," presented at Aug. 8-24, 1990 meeting of Society of Magnetic Resonance in Medicine, New York.

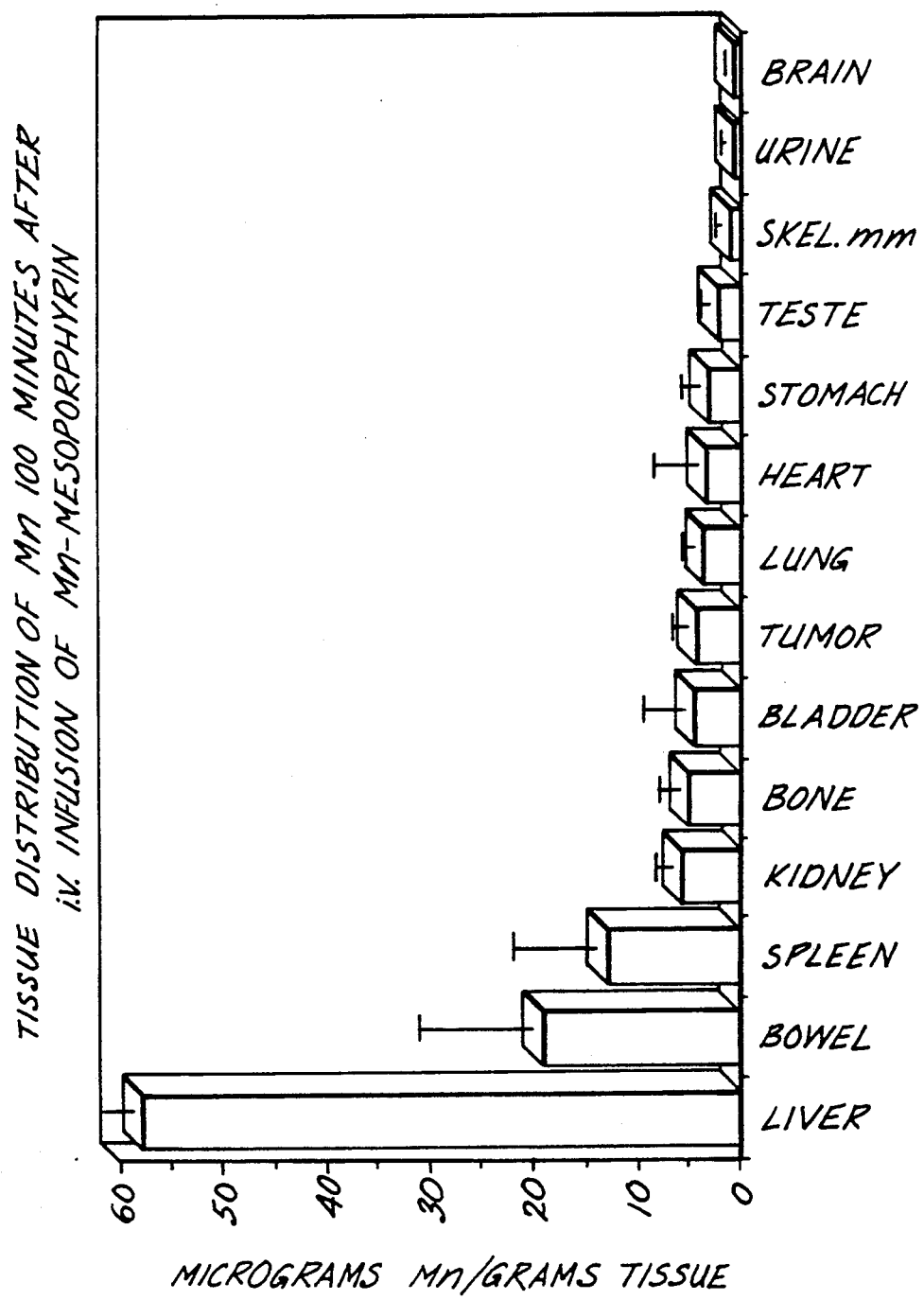

METHODS AND COMPOSITIONS FOR THE ENTERAL ADMINISTRATION OF HEPATOBILIARY MRI CONTRAST AGENTS

FIELD OF THE INVENTION

This invention relates to diagnostic imaging agents, and more particularly to improved methods and compositions for the enteral administration of contrast enhancing, magnetic resonance imaging agent in hepatobiliary diagnostic procedures.

BACKGROUND OF THE INVENTION

Metastatic liver disease is an important manifestation of many malignancies, particularly of the gastrointestinal tract (colon, pancreas) and with other tumors such as malignant melanoma. Colon cancer is the second leading cause of death in non-smoking males (Rice, RP, 1990), and accurate staging is essential for optimal humane management of victims of this disease. Similarly, accurate staging of pancreatic adenocarcinoma is important to minimize unncessary surgery for patients with spread of tumor to the liver. Diseases of the biliary track are also extremely common, with stones and inflammation as well as tumors involving the bile ducts and gallbladder. Thus, diagnostic visualization of the liver and bile ducts is one of the most common and important tasks of the diagnostic radiologist working in the field of abdominal radiology.

During the last decade, computed tomography (CT) has been the method of choice to detect and characterize focal disease of the liver, despite its limitations (Freeny, PC, et al 1983, 1986; see "Literature Cited", supra). Although several studies have demonstrated that the intravenous bolus administration of iodinated contrast agents does improve the sensitivity of CT to detect individual liver lesions, the overall efficacy and practicality of this approach has been felt to be less than ideal for the workup of patients with suspected focal liver lesions (Heiken, JP, et al, 1989). Because of the physical requirement of x-ray imaging, gram quantities of iodinated material are required for useful contrast enhancement. Hepatorophic, lipid soluble, radiographic contrast molecules have been more toxic than the more widely used water soluble agents, and have been better tolerated as oral dose forms (Lasser, EC, 1967). It is well known that these agents do not sufficiently concentrate in the liver to provide CT contrast enhancement.

Ultrasound is commonly used as a screening technique to evaluate for biliary tract and gallbladder stones, but ductal obstruction usually has to be evaluated with radioisotopic nuclear medicine scans (using, e.g., $^{99m}$Tc-HIDA, an immidoacetic acid complex), and use of invasive techniques such as endoscopic retrograde pancreatocholangiography (ERCP) or percutaneous transhepatic cholangiography. The only current technique for visualizing both the hepatic parenchyma and the biliary collecting structures simultaneously is the nuclear scan.

Recently, magnetic resonance imaging (MRI) of focal liver lesions has received considerable attention (Heiken JP, et al, 1989; Schmiedel U, et al, 1990; Stark, DD, et al., 1987, 1988). Several studies have shown that the sensitivity of a liver MRI study using multiple pulse sequences for detecting individual metastatic deposits was only 64%, which is somewhat higher than 51% reported in one study for contrast enhanced CT (Stark, DD, et al, 1987).

MRI techniques for visualizing liver parenchymal pathology are evolving rapidly, with increasing scan speeds allowing single breath hold or even more rapid images to be obtained of the liver with contrast characteristics making the procedures competitive with contrast enhanced CAT scanning (Mirowitz SA, 1990). However, sensitivity of both imaging modalities with the use of intravenous contrast material remains limited (Heiken JP et al., 1989).

With the advent of modern MRI imaging, allowing contrast discrimination of about 500 times that of x-ray, new possibilities for contrast media development arise. For example, effective contrast enhancement may be achieved with chemicals that would be too toxic in the dose range needed for radiography (Runge, VM, et al., 1983). MRI provides methods to obtain sophisticated chemical information from the living body non-invasively. Important additional contrast information can be obtained by varying the NMR pulse sequence. Causing tissue specific contrast enhancement with a fixed imaging sequence is important for refining the contrast sensitivity of such a sequence, and may speed up the imaging procedure and aid in MRI image guided intervention. Although "ideal characteristics" of an NMR contrast agent have been discussed (Brasch RC, 1982), these can vary with the task at hand. For interventional work, persistence of contrast enhancement is an advantage. For evaluation of renal function, fast renal excretion would be preferred. Current diagnostic evaluation of the liver and urinary system depends upon a mixture of techniques and procedures utilizing ultrasound, x-ray, computerized tomography, and nuclear medicine. Positive prolonged contrast enhancement of the liver and extrahepatic binary collecting structures, heretofore unavailable in the art, would be an ideal use of a contrast agent in the clinical setting.

Various contrast agents for liver MRI enhancement have been investigated, but known procedures and agents remain less than optimal. For example, the usefulness of gadopentetate dimeglumine (also known as "Gd-DTPA", and commercially available under the name Magnevist, from Berlix, N.J.), a water soluble, extracellular fluid MRI contrast agent for the assessment of focal liver lesions remains equivocal (Mirowitz et al., 1990, Schmiedl U. et al 1990). Gd-DTPA, by a mechanism similar to conventional iodinated contrast agents, rapidly equilibrates with the interstitial fluid space in both normal liver and pathological tissue following intravenous administration and nonselectively enhances either normal liver, focal liver lesions or both, depending on the timing of the image acquisition with the contrast media administration. In addition, Gd-BOPTA, a lipophilic gadolinium chelate which undergoes hepatic excretion and opacifies the bile ducts has recently been described and studied (Patrizio G et al, 1990), but there has been little work to ascertain its stability.

An alternative approach to contrast enhancement of the liver is the use of particulate agents for MRI, largely because particulate agents are selectively taken up into normal reticuloendothelial (RE) tissues. These materials, consisting of iron-oxide particles of various sizes are currently being evaluated as intravenous contrast agents to improve the sensitivity of MRI towards detection of focal liver lesions (Stark, DD, et al, 1988; Majumdar, S., et al, 1990). Ferromagnetic particles are typically used as "negative" contrast agents, i.e. they highlight a lesion by decreasing the signal of normal liver parenchyma. The widespread use of iron oxide particles has been limited to date by concerns about acute and chronic toxicity. Furthermore, this approach does not permit evaluation of the biliary system, which is closely related to hepatocyte function and frequently also of concern in the workup of patients with liver disease. Another particle candidate is the paramagnetic liposome, as discussed by Unger, et al (1989).

Porphyrins and other naturally occurring, and synthetic metallochemicals (Morton KA, et al., 1988) are interesting candidates for evaluation as paramagnetic contrast media. Porphyrins have long been known to cause localized photosensitization of tumors and may cause radiosensitization of certain tumors (Spikes, JD, 1975; Thomson, JM et al, 1971). Since the compounds are also strong metal chelators, they provide the possibility of combining the localizing characteristics of the porphyrin with the paramagnetic or radiation absorption properties of chelated metals. Several groups have recently published studies on the use of selected manganese porphyrins as MRI contrast agents, most of this work being with water soluble substances for evaluation of tumor contrast enhancement. (Fiel, RJ, et al, 1987, 1990; Patronas, NJ, et al, 1987; Chen, C-W, et al, 1984; Ogan, MD, 1987). Lipid soluble manganese porphyrins such as protoporphyrin and mesoporphyrin have also been studied (Jackson, LS, et al, 1985; Nelson et al 1986, 1990), Much of the reported work relating to porphyrin contrast media is directed toward the water soluble synthetic prophyrin, manganese tetrakis-(4-sulfonatophenyl)porphyrin or MnTPPS$_4$ (Patronas, NJ, et al, 1987). Recently, Bohdiewicz, et al (1990), reported usign Mn-hematoporphyrin as a hepatobiliary agent, but from the extent of urinary excretion reported, the agent of Bohdiewicz, et al must have contained significant quantities of water soluble contaminants or have been at least partially converted to a water soluble metabolite.

Early work with protoporphyrin was complicated by poor solubility and apparent high toxicity, although tissue specific T1(inversion time) effects were clearly demonstrated in the liver (Jackson, LS, et al, 1985). Subsequent work, including limited imaging experiments, revealed that manganese protoporphyrin caused hepatic and biliary contrast enhancement while the more hydrophilic manganese uroporphyrin produced dramatic contrast effects in the kidneys and urine. Mn mesoporphyrin has also been evaluated for MRI contrast enhancement of brain gliomas (Nelson, 1987) and has been shown to provide contrast enhancement of normal hepatic tissue leading to improved diagnostic visualization of tumors and abscesses on T1 weighted MRI images at non-toxic doses (Nelson, JA, et al, Soc. Body Computed Tomography, 1990).

Although significant advances in MRI imaging have been made, significant problems in tissue specificity, bioavailability and toxicity remain. Successful identification of an enterally deliverable hepatobiliary specific MRI contrast agent would be of great significance in advancing the commonly encountered problem of localization and accurate staging of primary or metastatic hepatic malignancy, and in the diagnosis and management of the even more common problem of stones and inflammation in the bile ducts. A noninvasive, quantitative procedure for spatially accurate evaluation of liver function would also be a powerful new tool in the field of liver transplantation.

SUMMARY OF THE INVENTION

It has now been discovered that NMR relaxation times in the hepatobiliary magnetic resonance imaging of a human or animal subject can be altered, and MRI heptabiliary images can be significantly enhanced by enterally administering to the subject an effective amount of a suitable lipophilic contrast enhancing agent. The lipophilic contrast enhancing agents comprise a chelating ligand and a paramagnetic moiety, and preferably enhance the MRI signal intensity of normal hepatocytes, but not that of tumor tissue. Preferred chelating ligands include mesoprophyrins protoporphyrins, deuteroporphyrins, pheophorbides, pyropheophorbides and chlorin $e_6$. Preferred paramagnetic moieties include gadolinium (III), iron (III), manganese (II and III), chromium (III), copper (II), dysprosium (III), terbium (III), holmium (III), erbium (III), and europium (III). A presently particularly preferred lipophilic contrast enhancing agent of the invention is Mn mesoporphyrin.

The contrast enhancing agents of the invention have been found to be effective as hepatobiliary contrast agents when enterally administered to a subject, such as by oral administration, thereby providing a major logistical and practical advantage in diagnosis of both parenchymal liver disease (e.g., liver tumors and abcesses) and of the bile ducts (e.g., strictures, stone and duct obstructing tumors).

BRIEF DESCRIPTION OF THE DRAWINGS

FIG. 3 is a bar graph showing the tissue distribution of Mn in micrograms of Mn per grams of tissue, 100 minutes after i.v. administration of Mn mesoporphyrin to NZW rabbits as described in Example 3.

FIG. 4A shows relative signal intensity values for control (A, B) animals, and for Mn mesoporphyrin treated animals 1.5 hours (C), 2.5 hours (D), 4.5 hours (E) and 6 hours (F) post treatment.

Figure 7:
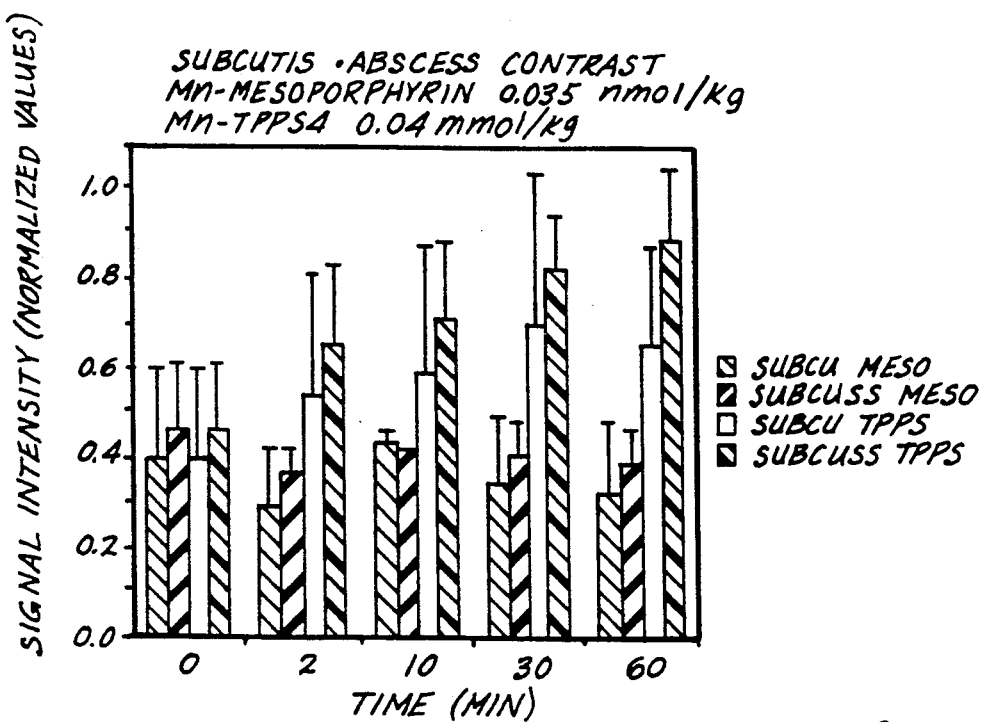

FIG. 7 is a bar graph of normalized MRI signal intensity in subcutis and subcutaneous liver abscess tissue following administration of Mn mesoporphyrin or TPPS$_4$ as described in Example 7.

Figure 8:
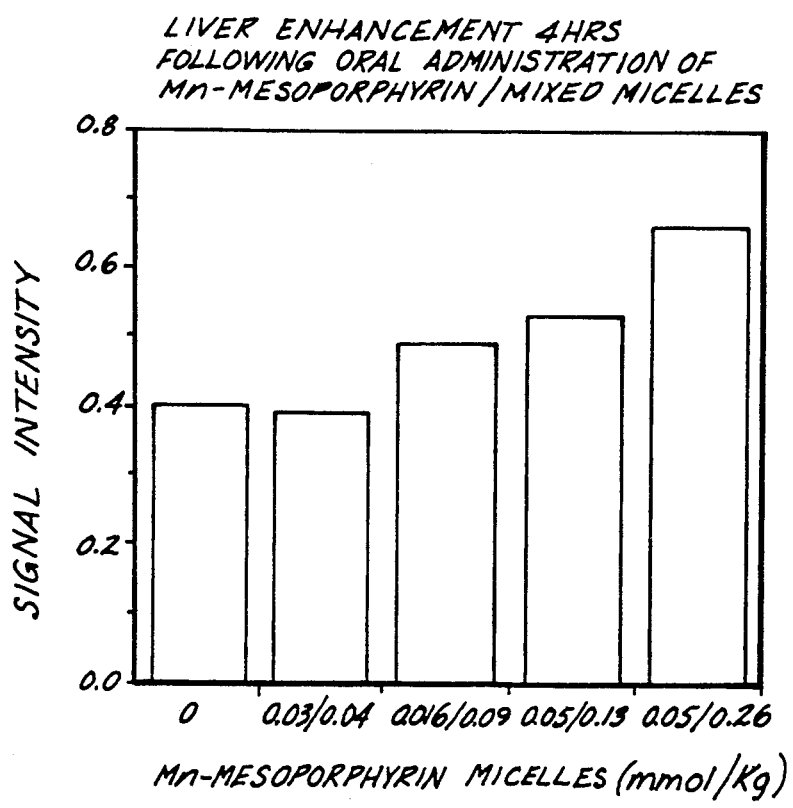

FIG. 8 is a bar graph of MRI signal intensity showing liver enhancement in rats following administration of varying concentrations of Mn mesoporphyrin/mixed micelle suspensions, as described in Example 8.

Figure 9A:
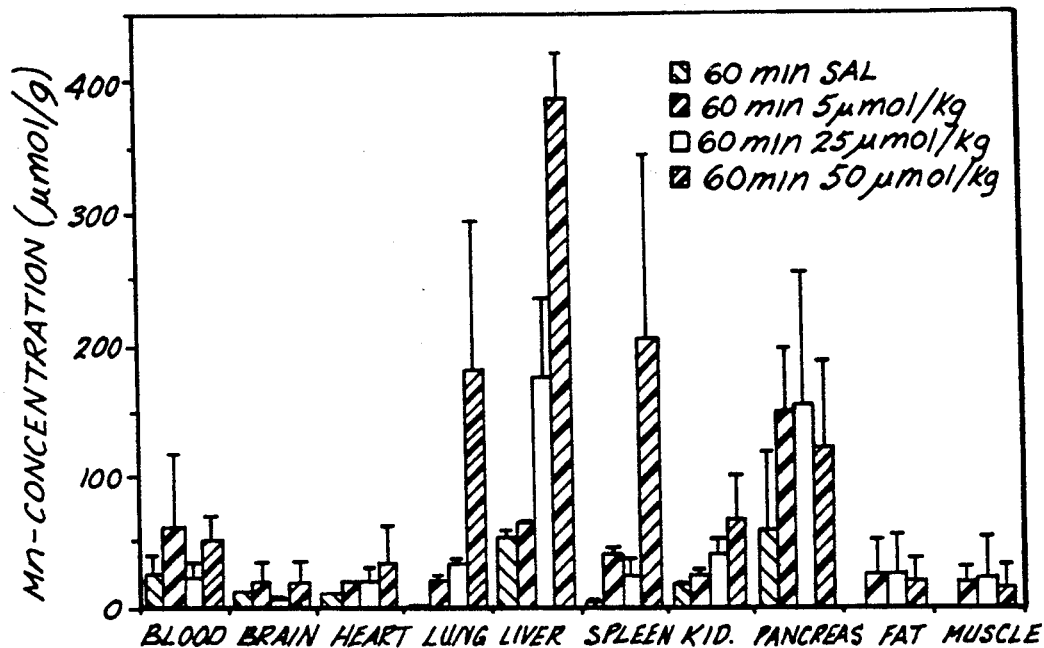
Figure 9B:
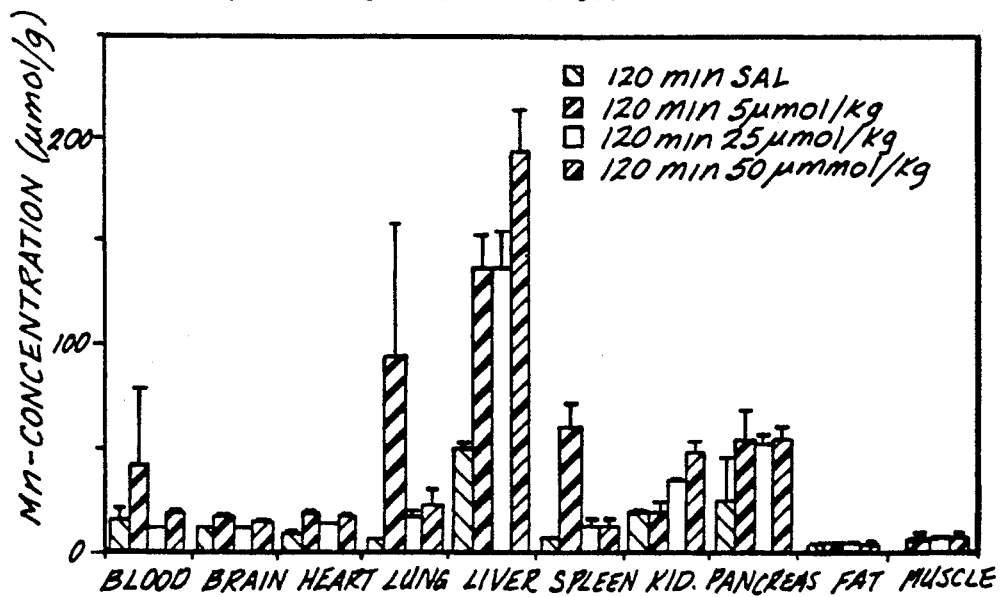

FIGS. 9A and 9B are bar graphs showing Mn concentrations in micromols per gram in various tissues at 60 minutes (FIG. 9A) or 120 minutes (FIG. 9B) following i.v. administration of 0 (sal, 0.005, 0.025 or 0.05 mmol/kg of Mn mesoporphyrin to normal rats as described in Example 9.

Figure 10:
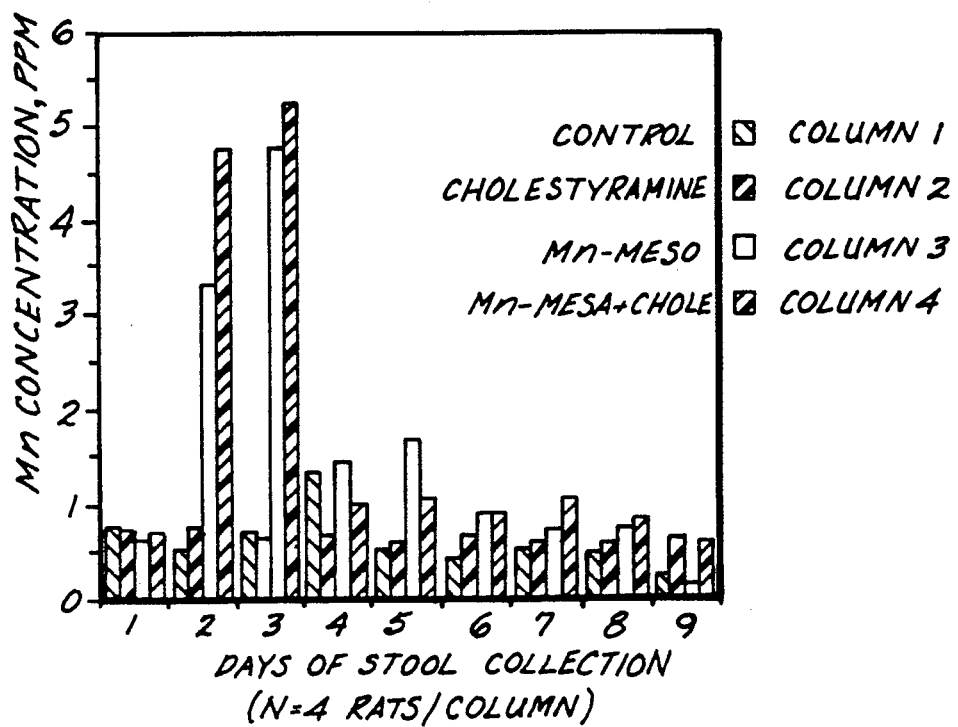

FIG. 10 is a bar graph showing the Mn concentration in parts per million in stool samples following cholestyramine, Mn mesoporphyrin, or cholestyramine plus Mn mesoporphyrin administration to rats, as described in Example 9.

DETAILED DESCRIPTION OF THE INVENTION

In accordance with one aspect of the present invention, a method is provided for altering NMR relaxation times in the heptabiliary magnetic resonance imaging of a human or animal subject, comprising enterally administering to the subject an effective amount of a lipophilic contrast enhancing agent. In one illustrative embodiment, the lipophilic contrast enhancing agent is orally administered to a subject together with a pharmaceutically acceptable enteric delivery agent.

As used herein, the term "lipophilic contrast enhancing agent" means any porphyrin compound having sufficient lipophilicity to be taken up preferentially by normally functioning hepatocytes as compared to liver or bile duct tumors and which is effective, on enteric administration in a suitable carrier to a human or animal subject, to lower the T1 relaxivity in the hepatocytes. Lipophilicity may be expressed in terms of an octanol:water partition coefficient, determined by introducing a contrast enhancing agent of the invention into a mixture of equal volumes of octanol and Tris buffer (e.g., 50 mM, pH 7.4) and then determining the relative amount of the contrast enhancing agent which partitions into each phase of the mixture. The lipophilic contrast enhancing agents of the invention have an octanol:water coefficient of at least about 2:1, more preferably at least about 5:1, and most preferably within the range of 10:1 to 30:1.

The lipophilic contrast enhancing agents of the invention include a chelating ligand, which provides the lipophilic properties of the agents and targets the agents to specific hepatic tissues to be imaged, and a paramagnetic substance, which provides the image enhancing properties of the agents. Presently particularly preferred chelating ligands include, for example, the mesoporphyrins, protoporphyrins, such as protoporphyrin IX, deuteroporphyrins, pheophorbides, pyropheophorbides and chlorin-e$_6$.

The paramagnetic portion of the contrast enhancing agents of the invention can be any paramagnetic ion of the transition metal or lanthanide series which has at least one, and more preferably five or more, unpaired electrons, and a magnetic moment of at least 1.7 Bohr magnetron. Suitable paramagnetic ions include, for example, gadolinium (III), iron (III), manganese (II and III), chromium (III), copper (II), dysprosium (III), terbium (III), holmium (III), erbium (III), and europium (III). The presently most preferred paramagnetic ions for this purpose are manganese (III) ions.

Preferably, the lipophilic contrast enhancing agents of the invention will have a low toxicity at the dosage levels employed. Preferred lipophilic contrast enhancing agents of the invention include, for example, manganese mesoporphyrin, manganese protoporphyrin, manganese deuteroporphyrin, manganese pheophorbide, manganese pyropheophoribide and manganese chlorin-e$_6$. The presently most preferred agent for this purpose is manganese (III) mesoporphyrin, sometimes referred to herein as Mn mesoporphyrin.

In contrast to hepatobiliary MRI enhancing agents known in the art which have required invasive intravenous administration, it is a key feature of the invention that the image enhancing agents of the invention may be administered enterally with retention of image enhancement properties. As used herein, the term enteral administration implies administration of the contrast agents in active and bioavailable form to the intestines of the subject to be imaged. Thus, the agents may be enterally administered orally, duodenally, rectally, by gastric lavage or by other methods providing delivery of the active agents to the intestines of the subject.

When administered orally, the lipophilic porphyrin agents of the invention precipitate in the stomach due to gastric acidity and remain in the stomach for prolonged periods of time, e.g., for 1 to 2 hours or longer. Accordingly, the compositions of the invention for oral administration comprise, in addition to the contrast enhancing agents, a pharmaceutically acceptable enteric delivery agent capable of protecting the contrast enhancing agents in the gastrointestinal environment, facilitating delivery of the manganese porphyrins to the intestine and enhancing bioavailability of the porphyrins to the liver and bile duct. In accordance with yet another aspect of the invention, lipophilic porphyrin compounds can be administered to a subject for purposes other than MRI contrast enhancement, such as for therapeutic treatment, provided that they are administered together with an enteric delivery agent as described herein. Thus, therapeutic porphyrins, such as Sn protoporphyrin may be orally administered in accordance with the present invention, instead being parenterally administered as required by prior art practices. Suitable enteric delivery agents for use in the practice of the invention include, for example, enteric coated capsules, tablets and pills, suppository base materials, and hydrophilic/lipophilic encapsulation systems such as liposomes and mixed micelles. In one presently particularly preferred embodiment, the carriers of the invention may comprise a micelle formulation, such as a formulation of taurocholate and monoolein, as will be further described below.

It has now been determined that, when administered together with a suitable enteric delivery agent, the image enhancing agents of the invention are capable of being enterally administered with image contrast enhancement heretofore obtainable only with intravenous injectable agents.

Solid dosage forms for oral administration include enterally coated capsules, tablets, pills, powders and granules. In such solid dosage forms, the lipophilic contrast enhancing agent is commonly admixed with at least one inert diluent such as sucrose, lactose or starch. Such dosage forms can also comprise, as in normal practice, additional substances other than inert diluent, e.g., lubricanting agents such as magnesium stearate. In the case of capsules, tablets and pills, the dosage forms may also comprise buffering agents.

Liquid dosage forms for oral administration include pharmaceutically acceptable emulsions, solutions, suspensions, syrups and elixirs containing inert diluents commonly used in the art, such as water, in which the contrast enhancing agents of the invention have been protected from deactivation in the stomach. Most commonly, the contrast enhancing agents will be protected from the stomach environment by a liquid form multiphase system, such a pharmaceutically acceptable micelle or liposome system. Alternatively, liquid based suspension of enterally coated solid phase microspheres or microcapsules may be employed for this purpose. Beside the active contrast enhancing agents and inert diluents, liquid based compositions may also include adjuvants, such as wetting agents, emulsifying and suspending agents, and sweetening, flavoring and perfuming agents, and other components known in the art.

Compositions for rectal administrations are preferably suppositories which may contain, in addition to the active agents, excipients such as cocoa butter or a suppository wax.

After enteral administration of the contrast enhancing agents of the invention, MRI imaging is carried out in a conventional manner. The choice of pulse sequence (inversion recovery, IR; and spin echo, SE) and the values of the imaging parameters (echo time, TE; inversion time, T1; and repetition time, TR) will be determined by the nature and environment of the tissue to be imaged and the diagnostic information sought, as is known in the art.

Actual dosage levels of the contrast enhancing agents of the invention may be varied so as to obtain optimal imaging characteristics under the conditions of employment of the compositions of the invention, while staying below the acute toxicity levels for the contrast enhancing agents employed. For most conditions, dosage levels of the contrast enhancing agents will range from about 0.1 to about 50 mg per kg of body weight of the subject to be treated, more preferably from about 0.5 to about 25 mg per kg of body weight, and most preferably from about 1 to about 10 mg per kg of body weight.

The foregoing may be better understood in connection with the following representative examples, which are presented for purposes of illustration and are not intended to limit the scope of the invention.

EXAMPLES

Example 1

Characterization of Mn Mesoporphyrin

Manganese mesoporphyrin chloride (MW=639.6 d; Porphyrin Products, Inc., Logan, Utah Lot #100990) was used to assess the lipophilicity and hydrophilicity of the compound by octanol:water partition coefficient determination. A sample of 1.0 mg Mg mesoporphyrin was added to 5.0 ml of 1-octanol and solubilized. To this was added 5.0 ml deionized water, and the solution was magnetically stirred for 24 hours, then centrifuged at 2000 rpm for 10 minutes. A 1.0 ml sample of water and 1-octanol were eluted from the solution, and a 5:1 dilution was performed on each in its solvent. Optical density was measured using a Beckman spectrophotometer at 550 nm (see below), and the ratio was calculated as the partition coefficient.

Stock solutions were prepared to test the stability of the compound in hydrophilic and lipophilic solvents and 0.100 g of the compound were solubilized in 0.5 ml 1N NaOH and 1.5 ml H$_2$O. To this was added 19 ml of 0.100 M K$_2$PO$_4$ solution, making a final volume of 21 ml. The solution was stirred for 10 minutes, then sonicated for 10 minutes, resulting in a dark brown, homogeneous solution free of precipitate. This was divided into five samples of 4.0 ml each, to which a varying amount of 1 N NaCl solution was added in order to achieve a final pH of 7.4, 8.0, 8.5, 9.5, and 12, respectively. A 1N NaCl solution was added to the tubes receiving less volume of base in order to control for ionic strength and final volume. The final volume of each sample was 8.0 ml, and the final concentration of Mn mesoporphyrin was $3.714 \times 10^{-3}$ M.

A separate stock solution of 0.100 g Mn mesoporphyrin in a solvent of 21.0 ml 100% ethanol was prepared in a similar fashion, but without the addition of H$_2$O. Final pH was achieved by addition of 1 N NaOH as before, but no correction was made for volume as the required amount of added base was less than 0.001 ml at each pH level. A third set of solutions were prepared using a solvent of 80% propylene glycol/20% ethanol in an identical fashion. Thus, the final concentrations of these solutions were $7.428 \times 10^{-3}$ M.

Finally, a stock solution was prepared using 0.100 g Mn mesoporphyrin in a solvent of 21.0 ml 10% DMSO in saline. Again, 1 N NaOH was added to titrate to the above pH levels, requiring volumes of less than 0.001 ml in each case, and the final concentration was also $7.428 \times 10^{-3}$ M.

All samples were stored for ten days in sealed test tubes placed in a dark cabinet at room temperature. Daily observations of color, character, and precipitate were made, followed by centrifugation at 2000 rpm for 10 minutes. An elution of 0.2 ml was pipetted from each sample daily, and was subjected to spectrophotometry at 550 mm (UV and visible absorption shows peaks at 390, 450, and 550 nm for Mn mesoporphyrin, with the greatest variation with concentration noted at 550 nm), followed by pH readings. Finally, atomic absorption data were obtained on the K$_2$PO$_4$ buffer solutions. Following each elution, the original sample was stirred for five minutes and sonicated for ten minutes before being returned to storage.

The octanol:water partition coefficient for Mn mesoporphyrin was 1.728:0.0665, resulting in a ratio of 25.98:1. Based on the results of the octanol:water partition coefficient, it is clear that the compound is highly lipophilic, and thus poorly soluble in any water-based solvent normally used for I.V. administration. Subsequent results from solubility tests in a K$_2$PO$_4$ buffer solution proved the compound is also basophilic, with improved solubility in high pH solutions.

Three known lipid solvent solutions were also investigated for solubility. A solution of 100% ethanol was found to have higher solubility for the mesoporphyrin than K$_2$PO$_4$, but poor buffering capacity. Propylene glycol/ethanol showed somewhat improved buffering characteristics over 100% ethanol, but a drift in proton concentration of ten fold was still observed. Finally, Mn mesoporphyrin was completely solubilized in a solution of 10% dimethyl sulfoxide (DMSO) in saline, with a smaller change in pH over time than the other two lipid solvents tested. These data indicate that among the agents investigated, solubility was highest in all instances at high pH, with only 10% DMSO exhibiting complete solubility at physiologic pH.

The significance of pH in injectable forms in toxicity is self-evident. While certain pharmaceuticals with high pH have approval for clinical use (i.e., Valium, pH 10), patients often complain of pain, burning, or stinging sensations localized to the area of the injected vessel immediately upon introduction. Further, rapid changes in local blood pH are capable of altering erythrocyte function and morphology, thus potentially leading to hemolysis. The significance of buffering capacity pertains to shelf life, and to stability of the compound. Ideally, a compound in solution would retain its chemical stability indefinitely, but this is rarely the case, as witnessed by many local anesthetic solutions which oxidize and lose effect after extended periods of time in solution.

Based on this study, water-based buffer systems at pH less than 10 are incapable of solubilizing Mn mesoporphyrin over any extended time frame, leading to precipitation despite excellent buffering characteristics. Of further note, the $K_2PO_4$ buffer solution itself would provide a bolus of potassium to the patient, thus potentially providing its own toxicity. Ethanol and propylene glycol/ethanol solutions exhibit improved solubility by optical density over the water-based buffer tested, but proton concentrations varied with extended shelf life. Finally, the 10% DMSO solution's excellent solubility and minimal pH fluctuation suggest it is the best potential vehicle tested. The mechanism of solubility of Mn mesoporphyrin in this compound is also unknown, and could impact on its potential use clinically if it alters the tissue distribution of the compound.

Thus, both hydrophilic buffer and lipophilic solvents shown excellent solubility for manganese mesoporphyrin at high pH; however, at physiologic proton concentrations 10% DMSO solutions appears to exhibit a higher degree of solubility, while precipitation was observed in $K_2PO_4$ buffer and ethanol-containing solutions.

Example 2

Portal and Venous Mn Concentration Following Oral Administration to Rabbits of Mn mesoporphyrin/Micelle Suspension Manganese Mesoporphyrin Solution 0.6006 mg of Mn mesoporphyrin chloride (Porphyrin Products, Inc., Logan, Utah) was dissolved in 4.2 ml of 1N NaCl and 7.8 ml of water, and the total volume of the solution was in increased to 126 ml by adding 114 ml of 0.1 M $K_2PO_4$ buffer (pH 7.00). The final pH was adjusted to 7.4(+ or −0.05) by titrating the solution with 1N NaCl and 1 N NaOH. The solution was kept in the dark for possible photosensitivity of the porphyrin products. The final Mn mesoporphyrin concentration was $7.45 \times 10^{-3}$ mmol/ml.

Monoolein/Taurocholic acid Solution (Micelle Solution)

Monoolein/Taurocholic acid Solution (Micelle Solution)

1.35 g of taurocholic acid was dissolved in 15 ml of de-ionized water and the volume of the solution was increased to 60 ml by adding more deionized water. Then, 0.89 mg of monoolein was slowly added to the solution over 20 mins. using an ice bath on a sonic mixer. The final monoolein and taurocholic acid concentration was 20 mM (the molecular weight of taurocholic acid is 537.7 g and that of monoolein is 356.5 g). The mixture was stored at 10° C.

Mn mesoporphyrin Micelle Solution

To obtain 0.1 mmol Mn mesoporphyrin per kg of rabbit body weight, 13.4 ml of the Mn mesoporphyrin solution/kg of rabbit body weight was measured (Mn mesoporphyrin concentration was $7.45 \times 10^{-3}$ mmol/ml). An equal volume of monoolein/taurocholic acid solution, described above, was added to the Mn mesoporphyrin solution and mixed over 15 mins with a sonic mixer (i.e., for a 5 kg rabbit, $13.4 \times 5 = 67$ ml of Mn mesoporphyrin solution with an equal volume of monoolein/taurocholic acid solution were mixed).

Figure 1:
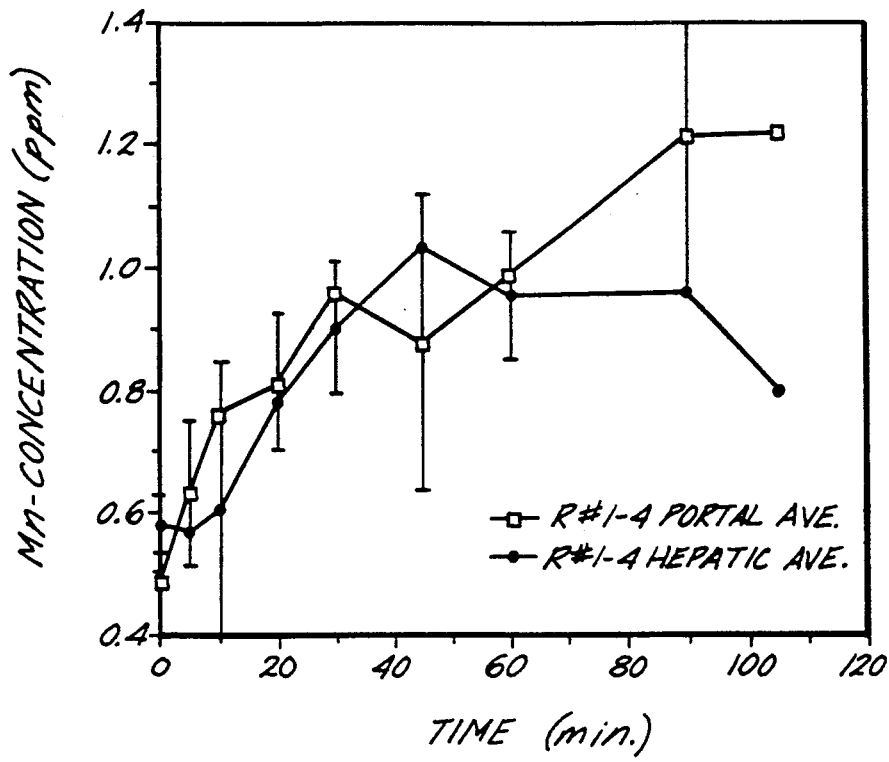
FIG. 1 is a graph of Mn concentration (in parts per million) in hepatic vein blood samples (indicated as solid diamonds) and portal vein blood samples (indicated as open boxes) as a function of time after oral administration of Mn mesoporphyrin to rabbits in accordance with the procedure of Example 2.

Procedure 6 adult New Zealand rabbits weighing between 3.8 and 4.6 kg were prepared by anesthesia and intubation, and the hepatic vein of each animal was catheterized under fluoroscopy guidance with a 5 gauge French catheter through the internal jugular vein. The portal vein of each animal was catheterized through an abdominal incision via the pyloric vein with a 3 gauge French catheter. A larger (5 gauge French) catheter was introduced into the distal duodenum and inserted 20 cm into the jejunum. 26.8 ml of the Mn mesoporphyrin/micelle solution described above per kg of rabbit body weight were injected into the intestines of each animal via the jejunal catheter. At 0, 5, 10, 20, 30, 45, 60 and 90 minutes post injection, blood samples were obtained from hepatic and portal veins, the blood samples were centrifuged, and the serum was separated for Mn mesoporphyrin measurement by atomic absorption spectrophotometer. The results are shown in FIG. 1, wherein data points from hepatic vein samples are shown as closed diamonds, and data points from portal vein samples are shown as open squares. At 0, 15, 30, 60 and 90 minutes post injection ("p.i."), urine sample collections were obtained, and at 0 and 90 minutes, bile samples were obtained. Manganese levels were measured using at atomic absorption spectrophotometer from the bile and urine samples. The results are shown in the following Table 1:

TABLE 1

| Rabbit No. | Bile and Urine Concentrations of Mn Mesoporphyrin (PPM) Following Oral Administration | | | | | | |
|---|---|---|---|---|---|---|---|
| | Urine (Mins p.i.) | | | | | Bile (Mins p.i.) | |
| | 0 | 15 | 30 | 60 | 90 | 0 | 90 |
| 1 | ND | 1.14 | 0.84 | 97 | 0.55 | ND | 1.44 |
| 2 | 0.43 | 0.44 | 0.39 | 0.36 | 0.36 | 0.8 | ND |
| 3 | 0.71 | 0.7 | ND | 0.88 | ND | 0.9 | 0.76 |

Two of the six rabbits were lost during intubation and surgery before obtaining any samples.

Example 3

Manganese-mesoporphyrin Experimental Vx-2 Carcinoma in NZW Rabbits: Imaging and Toxicity Studies.

Mn mesoporphyrin was studied as a hepatobiliary contrast agent for magnetic resonance imaging (MRI) usign the Vx-2 carcinoma model in New Zealand White (NZW) rabbits. The Vx-2 tumor is a rapidly growing anaplastic tumor which originally developed in the 1930's as a transformation of a papillomatous reaction following infection with the Shope virus in cottontail rabbits. In has since been maintained by serial passage in rabbit hind legs. The tumor is particularly well suited as a model of metastatic liver tumors because the rabbit hepatic artery anatomy resembles that of the human; the tumor grows well in the rabbit liver; and the hepatic Vx-2 tumor, like human liver metastasis, is supplied predominantly by the hepatic artery. The histology and grown characteristics of the tumor have been extensively described. Following implantation into soft tissue, the tumor enlarges rapidly and progresses, with locally increased vascularity in its outer rim. Characteristically, the rapid growth soon outstrips the blood supply, and the tumor undergoes central avascular necrosis. The animals eventually succumb to a combination of increased local and regional tumor burden, infection, and the growth of hematogenous metastasis in the lungs.

For this study, a NZW rabbit carrying a Vx-2 tumor in the subcutaneous tissue of a hind leg was obtained from A. G. Wile and D. Henderson-Snow, Dept. of Surgery, University of California, Irvine, Calif. The tumor line was maintained at the University of Washington, Seattle, Wash., by repeated passage into hind leg carriers, which provided n ongoing source of tumor tissue for surgical passage into the livers or rabbits. Injections into the liver of minced tumor tissue were made under direct visualization afforded by a small midline laparotomy following the procedure described by Swistel, JA, et al (1984), and Vx-2 tumor cell suspensions were prepared. Cell suspensions were used in this study for the transcatheter intra-hepatic artery embolization of $10^7$ tumor cells in 2 animals, as an additional model of tumor metastasis. Operative procedures were performed under sterile conditions, with intravenous ketamine and acepromazine as preanesthesia, and intravenous Suritol for general surgical anesthesia. To alleviate any possible postoperative pain, subcutaneous buprinophine was administered once each day through the fourth postoperative day.

Imaging

Using 13 rabbits carrying Vx-2 tumors implanted in the liver, the MRI signal intensity of normal liver tissue, Vx-2 tumor and the gall bladder at 0, 10, 20, 30, 60 and 90 minutes after the intravenous administration of 0.04 mmol/kg of rabbit body weight (25 mg/kg) Mn mesoporphyrin was measured, as is hereinafter further described. For gross correlation of tumor size and distribution for comparison with MR images, these animals were then sacrificed by barbituate overdose, frozen at $-20°$ C., and transversely cross sectioned on a band saw. Transverse images of the rabbit abdomens were obtained using a General Electric CSI-II 2.0 T, 85.6-Mhz proton resonant frequency, chemical shift imaging spectrometer (GE Medical Systems, Fremont, Calif.), equipped with a 16 cm inner diameter, 28 cm long imaging coil of low-pass bird cage resonator design and a balanced-matched tuning network. A standard spin echo 2DFT sequence employing eight 3 mm thick slices, averaging four phase cycled signal acquisitions, using a TR of 265 msec and a TE of 14 msec was employed, generating a raw data matrix size of 128 phase-encoded cycles by 256 complex data points which was transposed to 256×256 image output pixels over a 120×120 mm field of view. The imaging sequence parameters and number of acquisitions averaged were chosen to minimize motion artifact. Eight rabbits were imaged at 10-14 days after tumor implantation. To expand the data base, five of the animals were imaged a second time 6 to 9 days later. By including these image acquisitions in the analysis, a total number of animal observations of 13 was achieved. Precontrast and postcontrast signal intensities were measured by region of interest (ROI) analysis from normal liver parenchyma, Vx-2 lesions, and the gallbladder. Signal intensities were averaged from two ROIs in each of these tissues. Efforts were made to avoid edge and partial volume artifacts. All measured signal intensities (SI) were normalized to the intensity of a vegetable oil (corn oil) standard, with enhancement then calculated according to the formula: (SI postcontrast−SI precontrast)/SI precontrast.

Contrast 0.150 g of chemically pure Mn mesoporphyrin (639.6 grams/mole) was used as obtained from Porphyrin Products (Logan, Utah) (Lot #100990). The solubility of this compound was found to be pH dependent, with solutions being most stable when stored at high pH (greater than 10), and titrated to pH 7.5-7.6 prior to administration. Solutions were prepared by first completely dissolving 0.100 grams of Mn mesoporphyrin in 2 ml 0.5 N NaOH, and then adding 19 ml of 0.054 M $NaHCO_3$ in normal saline, or 19 ml of an isotonic $KPO_4$ buffered saline solution, yielding a 7.40 mM solution of Mn mesoporphyrin. The study was initiated using the potassium phosphate buffer, which was latter abandoned, and substituted by sodium bicarbonate buffer at it was felt to be potentially toxic (potassium overload of animals). Prior to administration of the mixture, the pH was adjusted with 1 N HCL, as described above. The solution was passed through a 2 micrometer millipore filter. The amount of the contrast agent left behind in the filter was negligible. To achieve a dose of 0.04 mmol/kg, an average of 17 cc of this solution was administered through a butterfly needle into an ear vein of animals which ranged around 3.5 kg in weight. The animals were prepared for imaging with ketamine and acepromazine preanesthetic, and maintained under a light general anesthesia with intravenous Suritol. Images were obtained prior to injection of the contrast agent, and 10, 20, 30, 60 and 90 minutes after its infusion. The animals were then euthanized by intravenous Suritol overdose followed by 10 cc of a saturated KCl solution. The whole animal was immediately frozen at $-20°$ C. degrees and, after several days, cross sectioned transversely for gross correlation of tumor morphology.

Figure 2:
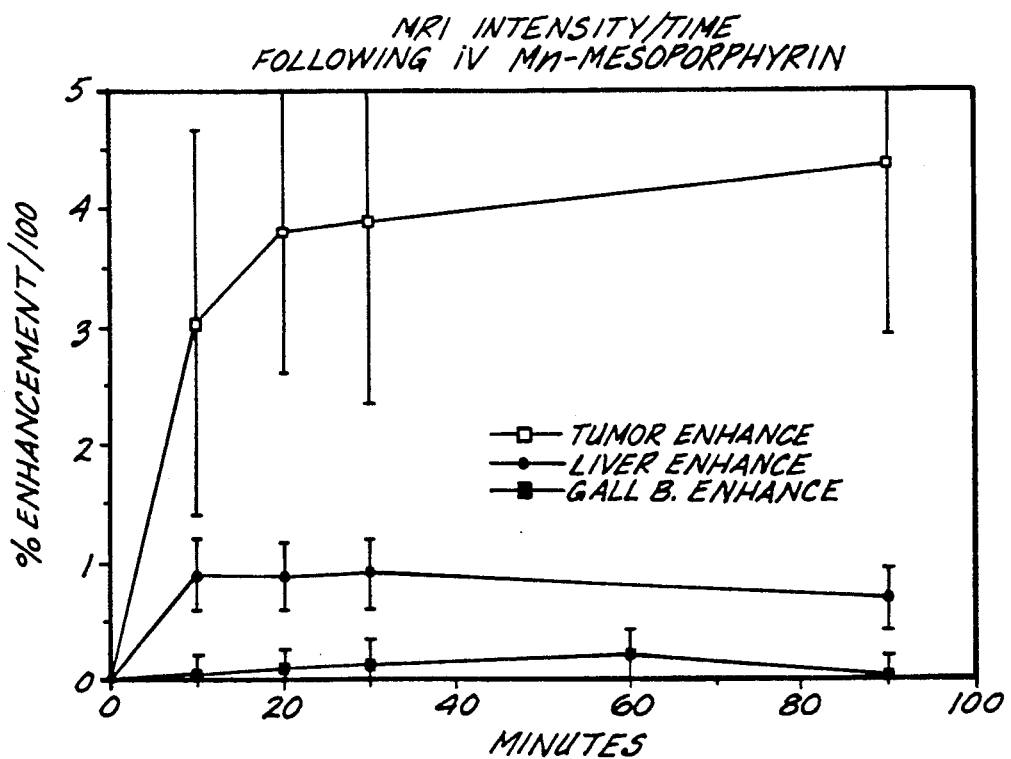
FIG. 2 is a graph of the percentage enhancement of MRI signal intensity in liver (closed diamonds), gall bladder (closed boxes) and tumor tissue (open boxes) as a function of time following i.v. administration of Mn mesoporphyrin to New Zealand White (NZW) rabbits as described in Example 3.

As shown in FIG. 2, at an intravenous dose of 0.04 mmol/kg Mn-mesoporphyrin produced enhancement of normal liver tissue (shown as closed diamonds in FIG. 2) and the gall bladder (shown as closed squares in FIG. 2), but not of Vx-2tumor tissue (shown as open squares in FIG. 2). This impression was supported by region of interest intensity measurements which showed 89.6+/−17.5% enhancement of the liver, 373+/−92.3% enhancement of the gall bladder, but only 12.7+/−12.1% enhancement of the tumor tissue at 30 minutes after administration of the contrast agent. The tumor enhancement was not statistically significant.

Tissue Distribution

To determine the tissue distribution of Mn mesoporphyrin in these animals at 100 minutes after administration of the compound, several tissues were harvested from each animal and manganese content was determined by atomic absorption spectrophotometry of nitric acid digested samples, yielding an approximation of Mn mesoporphyrin distribution among various tissues, including normal liver, Vx-2 tumor tissue, spleen, brain, lung small bowel, bladder, heart, stomach, skeletal muscle, bone and bladder urine. The results are shown in FIG. 3 from which it is apparent that Mn mesoporphyrin was highly concentrated in the liver with lesser amounts in the bowel and spleen tissue.

Acute Toxicity Study

A preliminary acute toxicity study was performed, in which the serum bilirubin, liver enzymes, and electrolytes in 6 rabbits were followed over a five day period after the intravenous administration of 0.04 mmol/kg of Mn mesoporphyrin. For this study, 8 normal NZW rabbits were anesthetized with preanesthesia as described above. After 3 of whole blood was obtained from each animal, 6 of the animals were given an intravenous dose of 0.04 mmol/kg Mn mesoporphyrin, while 2 animals received an identical volume of buffer solution without Mn mesoporphyrin. The aninmals were recovered, and again anesthetized and subjected to 3 ml blood draws on days 1, 3, and 7. Serum levels followed included: bilirubin, sodium, potassium, chloride, BUN, $CO_2$, creatinine, glucose, SGOT, SGPT, LDH, alkaline phosphatase and amylase. In addition, each animal's temperature was recorded at each blood draw, and the animal's eating and drinking habits were observed daily. The results are shown as average figures in the following Table 2:

TABLE 2

Mn Mesoporphyrin Toxicity

| | Controls | | | | Mn Mesoporphyrin Treated | | | |
|---|---|---|---|---|---|---|---|---|
| | Day 0 | Day 1 | Day 3 | Day 7 | Day 0 | Day 1 | Day 3 | Day 7 |
| BUN | 25.5 | 26 | 25 | 28 | 26.33 | 25.17 | 26.67 | 24.33 |
| $Na^+$ | 137 | 142 | 139.5 | 138.5 | 137.17 | 140.67 | 140.5 | 134.17 |
| $K^+$ | 5.05 | 4.9 | 5.6 | 4.65 | 5.4 | 5.28 | 6.33 | 4.73 |
| $Cl^-$ | 104 | 108.5 | 104.5 | 105 | 101.83 | 104.5 | 103.33 | 99.67 |
| Glucose | 106 | 123.5 | 183.5 | 163.5 | 107.67 | 122.83 | 169.33 | 139.67 |
| $CO_2$ | 21 | 18 | 22.5 | 20.5 | 22.17 | 21.67 | 21.83 | 22 |
| GAP | 12 | 15.5 | 12.5 | 13 | 13.17 | 14.5 | 15.33 | 12.5 |
| CRT | 0.9 | 0.9 | 1 | 1.05 | 0.97 | .083 | 1.13 | 0.98 |
| Bilirubin | 0.3 | 0.25 | 0.3 | 0.2 | 0.23 | 0.18 | 0.37 | 0.25 |
| Alk. Phos. | 47 | 48.5 | 46 | 39.5 | 58 | 57.33 | 58.17 | 49.17 |
| GPT | 44 | 62 | 62.5 | 44.5 | 42 | 48.5 | 55.33 | 44.5 |
| GOT | 19 | 24.5 | 14.5 | 12 | 15.83 | 12.5 | 23.33 | 11.33 |
| Amylase | 153 | 170.5 | 163.5 | 142.5 | 174.67 | 222.67 | 212.17 | 189 |
| LDH | 670.5 | 587.5 | 423 | 467.5 | 593.83 | 1026 | 414.83 | 275 |

As shown in Table 2, no significant systematic changes occurred in the laboratory values of 6 rabbits that had received Mn mesoporphyrin and those of 2 controls which had received an identical volume of buffer solution without Mn mesoporphyrin. Combined with the imaging contrast data, above, these results demonstrate the utility of this compound as a safe and effective agent for the MRI enhancement of normal liver tissue and the biliary system.

Example 4

Enhanced Hepatic Imaging Following Oral Administration of Mn Mesoporphyrin to Rats Manganese Mesoporphyrin 0.2005 mg of Mn mesoporphyrin chloride (Porphyrin Products, Inc., Logan, Utah) was dissolved in 1.4 ml of 1N NaCl and 2.6 ml of water. The total volume was increased to 40 ml by adding 36 ml of 0.1 M $K_2PO_4$ buffer (pH 7.00). The final pH was adjusted to 7.4(+ or −0.05) by titrating the solution with 1 N NaOH. The solution was kept in the dark for possible photosensitivity of the porphyrin products. The final Mn mesoporphyrin concentration was $7.34 \times 10^{-3}$ mmol/ml. This volume is sufficient for approximately 10 rats (200–250 g).

Monoolein/Taurocholic acid Solution (Micelle Solution)

860 mg of taurocholic acid was dissolved in 40 ml of de-ionized water. Then, 570.6 mg of monoolein was slowly added to the taurocholic acid solution using an ice bath on a sonic mixer. The final monolein and taurocholic acid concentration was 40 mM (the molecular weight of taurocholic acid is 537.7 and that of monoolein is 356.5). The mixture was stored at 10° C. until used.

Mn-Mesoporphyrin/Micelle Solution

To obtain 0.1 mmol Mn mesoporphyrin per kg of rat body weight, 13.4 ml of Mn mesoporphyrin/kg of rat weight was measured (for example, 2.7 ml for a 200 g rat). An equal volume of monoolein/taurocholic acid solution was added and mixed over 15 mins with a sonic mixer. The final micelle concentration was 20 mM.

Feeding and Imaging

Figure 4A:
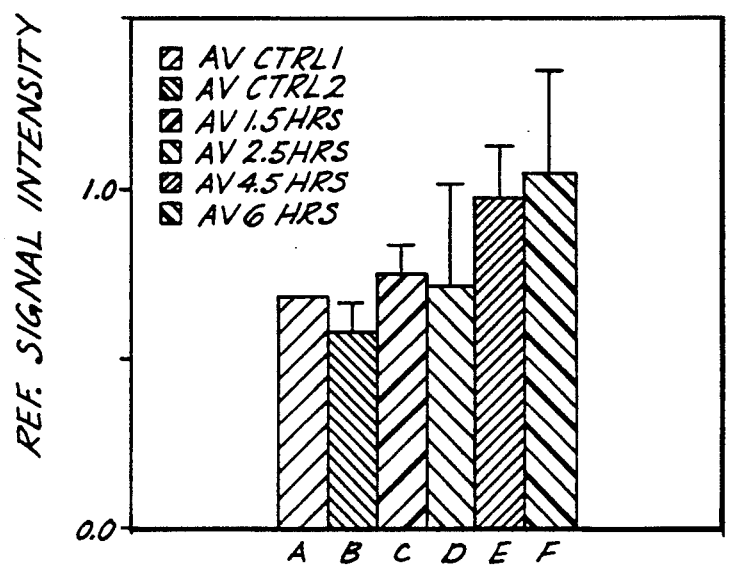
FIG. 4A is a bar graph of relative MRI signal intensity from hepatic tissue after oral feeding of rats with a Mn mesoporphyrin/mixed micelle suspension as described in Example 4.
Figure 4B:
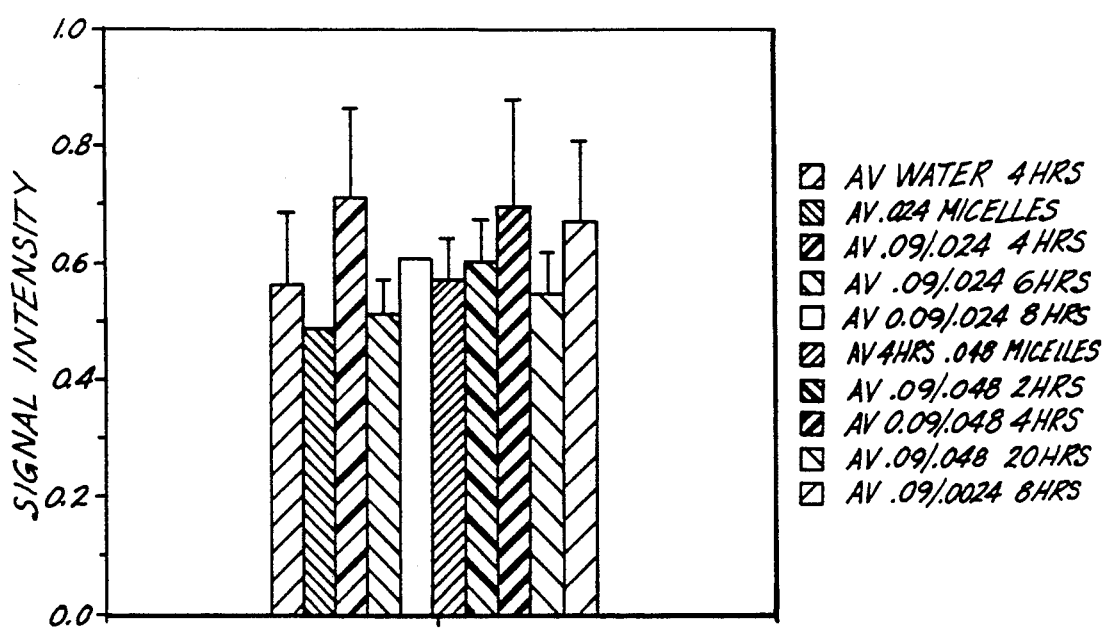
FIG. 4B is a comparative bar graph showing similar data for animals which had been treated with an ineffective Mn mesoporphyrin/mixed micelle suspension, as described in Example 4.

Groups of 3 rats each were fed orally with 26.8 ml/kg of rat bodyweight of the Mn mesoporphyrin/mixed micelle solution at 2, 4, 6, and 8 hours before imaging. Two control groups of rats (2 rats each) that received an equal volume of micelles/water or water only were also imaged at 4 hrs p.o. Imaging was performed with a General Electric CSI-II 2.0 T (85.6 MHz proton resonant frequency) chemical shift imaging spectrometer (GE Medical Systems, Fremont, Calif.). The proton imaging sequence used throughout this study was that a standard pin echo 2DFT sequence that employed a single 3 mm slice thickness with four phase cycled signal acquisitions. The raw data matrix size was 128 phase-encoding cycles by 256 complex data points (quadrature detection mode) transposed to 256×256 image output pixels over a 100×100 mm field of view (FOV). Coronal images were obtained of the rats' abdomen and thorax using a TR of 160 msec and a TE of 16 msec. A specially designed 53 mm outer diameter (130 mm long) imaging coil of the low-pass birdcage resonator design was employed with a balanced-matched tuning network for all images. This design allowed for near complete coil filling with excellent sensitivity and B1 homogeneity over the images volume. All parameters were held constant for the imaging protocol. Signal intensity was measured by region-of-interest (ROI) analysis both for normal liver parenchyma, liver lesions and the corn oil standard. Signal intensity from normal liver was averaged from two ROIs. One ROI was placed over the center and the periphery of the hepatic metastases, respectively. Signal intensities were also determined for normal subcutaneous tissue in the area of the thoracic wall and for subcutaneous abscesses located in the anterior abdominal wall in rats with liver abscesses. Measured signal intensities were normalized to the intensity of the corn oil standard for all pre- and postcontrast images. Signal intensity (SI) enhancement was calculated according to the formula: (SI postcontrast−SI precontrast)/SI precontrast. The average relative signal intensity of each group is shown in FIG. 4A. For purposes of comparison, the foregoing procedure was repeated, except that the micelle solution was not cooled during formulation, resulting in the failure of formation of enterally protected micelles. The results are shown in FIG. 4B, were a lack of statistically significant liver tissue signal enhancement is apparent.

Example 5

Liver Enhancement in Normal and Liver Abscess Rats After I.V Administration

Pyrogenic liver abscesses were induced in Sprague-Dawley rats following the method of Weinsten, WM, 1975. Twelve female sprague-Dawley rats (250-300 g each) underwent midline laparotomy following intraperitoneal anesthesia with sodium pentobarbital (40-50 mg/kg), and a filtered bacterial inoculum of colonic contents was directly injected into the liver of each rat. Two animals died within 24 hours following surgery and were excluded from the study. The remaining 10 rats underwent MR imaging 4-6 days after surgery, as described below. 5 rats received Mn mesoporphyrin as a contrast enhancing agent, and 5 rats received Mn TPPS$_4$ for purposes of comparison as follows.

0.1523 g Mn-TPPS$_4$(MG=1062 d, Porphyrin Products, Inc., Logan, Utah) were dissolved in 0.5 ml 1 N NaOH, 1.5 ml H$_2$O, and 19 ml 0.1 M K$_2$HPO$_4$ buffer, pH 7.4. The concentration of this stock solution was $7.48 \times 10^{-3}$ M. 0.1001 g Mn mesoporphyrin (MG=693 d, Porphyrin Products, Inc., Logan, Utah) were dissolved in the identical solution to yield a concentration of 7.429 $10^{-3}$ M. The solutions were filtered through a 2 micrometer millipore filter. The T1relaxivity of Mn mesoporphyrin (R1) is 6 L (mmol/sec$^{-1}$) as measured by field cycling at 35° C. (S. Koenig, IBM Watson Lab).

Dose

Rats (n=5 per dose) were administered an intravenous dose of 0.035-0.045 mmol/kg of Mn mesoporphyrin. These studies were done at an estimated 1/10 of the LD$_{50}$ of protoporphyrin (Jackson et al, 1985). To compare Mn mesoporphyrin image enhancement to that of Mn-TPPS$_4$, rats with bacterial liver abcesses (n=5) were administered 0.040 mg Mn TPPS$_4$ per kg of body weight.

All rats inoculated with fecal material developed intrahepatic abscesses and, due to seeding at the site of surgery, subcutaneous abscesses. Two rats of the ten rats died following the imaging experiment. One rat had received Mn TPPS$_4$ and one Mn mesoporphyrin. In was unclear from the experiment whether the animals died due to the contrast media administration or due to effects of anesthesia. Liver abscesses were slightly hypointense compared to normal liver parenchyma on T1 weighted precontrast images.

Imaging experiments were performed with a General Electric CSI-II 2.0 T (85.6 Mhz proton resonant frequency) chemical shift imaging spectrometer (GE Medical Systems, Fremont, Calif.). The proton imaging sequence used was that of a standard pin echo 2DFT sequence that employed a single 3 mm slice thickness with four phase cycled signal acquisitions. The raw data matrix size was 128 phase-encoding cycles by 256 complex data points (quadrature detection mode) transposed to $256 \times 256$ image output pixels over a $100 \times 100$ mm field of view (FOV). Coronal images were obtained of the rats+ abdomen and thorax using a TR of 160 msec and a TE of 16 msec. A specially designed 53 mm outer diameter (130 mm long) imaging coil of the low-pass birdcage resonantor design was employed with a balanced-matched tuning network for all images. This design allowed for near complete coil filling with excellent sensitivity and B1 homogeneity over the images volume.

Signal intensity was measured by region-of-interest (ROI) analysis both for normal liver parenchyma, liver lesions and a corn oil standard. Signal intensity from normal liver was averaged from two ROIs. One ROI was placed over the center and the periphery of the hepatic metastases, respectively. Signal intensity was measured over the center of the hepatic abscesses. Signal intensities were also determined for normal subcutaneous tissue in the area of the thoracic wall and for subcutaneous abscesses located in the anterior abdominal wall in rats with liver abscesses. Measured signal intensities (SI) were normalized to the intensity of the corn oil standard for all pre- and postcontrast images. Signal intensity enhancement was calculated according to the formula: (SI postcontrast−SI precontrast)/SI precontrast. The results are shown in FIG. 5, in which normalized signal intensity is shown as a function of time post injection.

Figure 5:
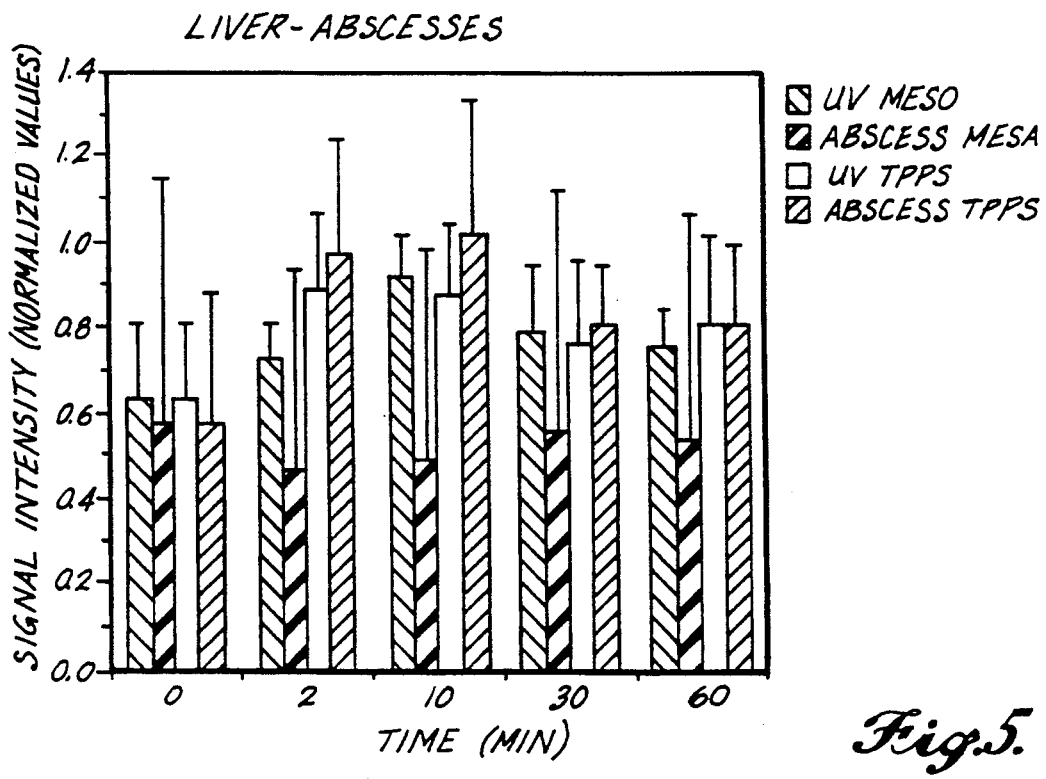
FIG. 5 is a graph showing MRI signal intensity (normalized to corn oil) in hepatic tissue as a function of time after i.v. administration of Mn mesoporphyrin or Mn TPPS$_4$ to normal or liver abscess rats as described in Example 5.

Referring to FIG. 5, at 10 minutes post injection, Mn TPPS$_4$ yielded enhancement of normal liver parenchyma and abscess by 43% (p greater than 0.05) and 63% (p less than 0.05), respectively. Mn mesoporphyrin also yielded liver enhancement by 43% (p less than 0.01) at 10 minutes. Liver abscesses were, however, not enhanced at any time using this contrast media. Subcutaneous abscesses were seen as tumors of the anterior abdominal wall with heterogeneous signal intensity on precontrast images. Following administration of Mn TPPS$_4$, subcutaneous abscesses and normal subcutaneous tissue were enhanced by 88% (p greater than 0.05) and 56% (p less than 0.05), respectively, at 60 minutes. Mn mesoporphyrin did not yield enhancement of normal subcutis and subcutaneous abscesses. As shown in FIG. 5, Mn mesoporphyrin administration causes significant (30-50%) and prolonged enhancement of normal liver parenchyma over the observation period of 60 min. However, Mn-TPPS$_4$ enhanced both normal liver and abscesses, thus providing no improved contrast between normal and diseased tissue.

Pathological examination revealed chronic liver abscesses characterized by a central cavity filled with amorphous proteinaceous material, surrounded by a rim of infarcted parenchyma which included bacterial colonies. The rim of infarcted parenchyma itself was surrounded by a rim of dense neutrophil inflammation and finally by a rim of granulation tissue. Abscess size range from 2-3 mm up to 10 mm. Specimen of the anterior abdominal wall in the area of the suture showed multiple abscesses within the subcutaneous fat and connective tissue, skeletal muscle intercostal connective tissue, and deep adipose tissue.

Example 6

Liver metastases

Following the procedure of Example 5, the MRI enhancement properties of Mn mesoporphyrin were compared to Mn-TPPS$_4$ in rats with liver metastases (breast adenocarcinoma), and found to exhibit a similar pattern as was found as in rats with liver abscesses. For this experiment, 19 Fischer 344 female rats (Charles River Laboratories, Wilmington, Mass.), weighing 150-200 g each were used for tumor implantation following the procedure of Saini et al, 1987. A mammary adenocarcinoma (R3230 AC) cell line was acquired from the Breast Cancer Animal and Human Tumor Bank of the National Cancer Institute (EG&G Mason Research Institute, Worcester, Mass.). The tumor was maintained by repeated flank implantation and harvested for liver implantation. After complete excision of the flank tumors (1-2 cm in diameter) 1 mm$^3$ fragments were obtained from the tumor perimeter. A midline laparotomy was performed on rats under pentobarbital anesthesia and tumor fragments were inoculated immediately into the parenchyma of an exposed anterior lobe of the liver using a 18 gauge needle. Hemostatis was achieved by gently compressing the puncture site with surgical gaze and the abdomen was closed with a two layer suture. The entire procedure was performed under sterile conditions. Four animals died within 48 hours following surgery. The remaining 15 rats underwent MR imaging between 16 and 21 days after liver implantation. 9 rats received Mn mesoporphyrin, and 6 rats received Mn TPPS$_4$.

All rats implanted with tumor cells developed liver metastases at the site of implantation. Liver metastases ranged from 1-2 mm diameter to 2 cm diameter. Histological examination following H&E staining showed that the tumor cells were arranged in glands and sheets, and were fairly well differentiated and relatively monotonous. Many cells had intracytoplasmatic vacuoles suggestive of mucin or secretory product production. Tumors over 2 cm in diameter typically had areas of central tumor necrosis. The tumor appearance was compatible with metastatic mammary adenocarbinoma.

Figure 6:
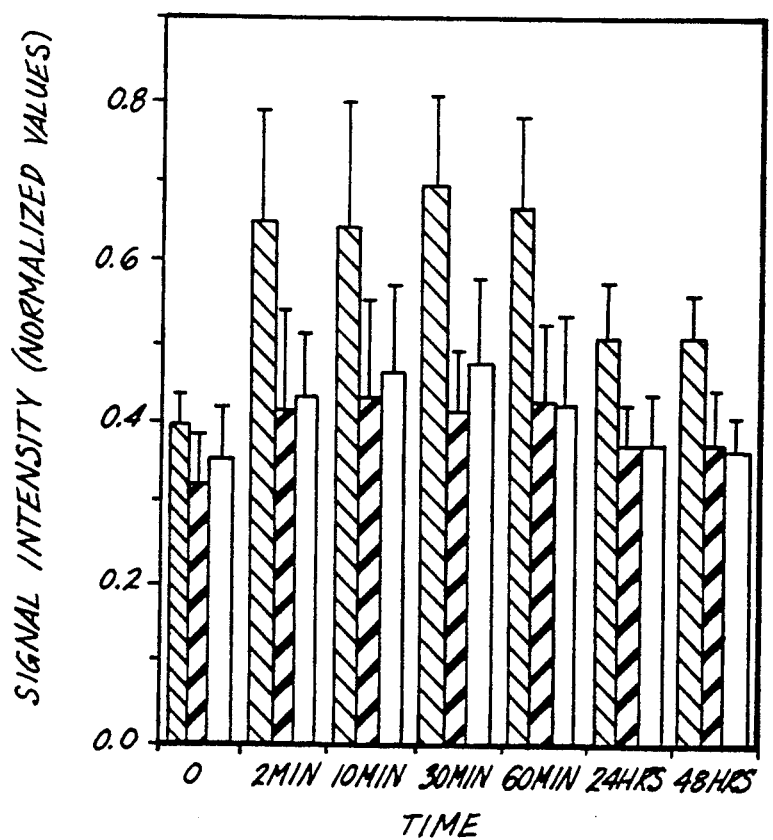
FIG. 6 is a bar graph showing the average MRI signal intensity of liver (Liv), tumor center (TuCe), and tumor periphery (TuPe) following i.v. administration of 0.035 mmol/kg of Mn mesoporphyrin to rats with liver metastases as described in Example 6.

The results are shown in FIG. 6, in which the average signal intensity of liver (Liv), tumor center (TuCe), and tumor periphery (TuPe) following i.v. administration of 0.035 mmol/kg manganese mesoporphyrin is plotted against time. The increased signal of the normal liver made visualization of tumor deposits extremely simple, and allowed identification of tumor deposits not clearly seen on the pre-contrast image. With TPPS$_4$, a general increase in signal intensity of both the normal liver and tumor failed to help in distinguishing the site of the tumor deposits. As further shown in FIG. 6, Mn mesoporphyrin preferentially enhanced normal liver parenchyma over 60 min (70% maximum enhancement), but did not significantly affect the signal intensity of metastases as measured over 2 regions-of-interest in the center and the periphery of the tumors (n=6 rats). At 24 and 48 hrs (n=3 rats) no delayed tumor enhancement was observed. The signal intensity of normal liver parenchyma was still increased by 30% over baseline at this time. This value may, however, be artificially high due to impaired metabolism of these rats that had a large tumor load (widespread metastatic disease) and were under pentobarbital anesthesia for a total of 15 hours (3 imaging experiments) during a 48 hour period. Mn-TPPS$_4$ enhanced both liver and tumor thus providing no discrimination of the lesion as compared to unenhanced images.

Example 7

Subcutaneous tissues

Following the procedure of Example 5, enhancement of normal subcutaneous tissue and subcutaneous abscesses was also studied in rats that had liver abscesses. Mn-TPPS$_4$ enhanced both subcutis and subcutaneous abscesses. This enhancement pattern has previously also been demonstrated with Gd-DTPA, a typical water soluble contrast agent. As shown in FIG. 7, Mn mesoporphyrin did not enhance either subcutis or subcutaneous abscesses. This pattern further supports the pharmacologically different distribution of the more lipid soluble porphyrin compared to the water soluble Mn-TPPS$_4$, and coincides with the separate observation that the color of the rats' skin did not change following administration of Mn mesoporphyrin whereas a green discoloration of the skin was noticed in rats following injection of Mn-TPPS$_4$. The lack of skin discoloration using Mn mesoporphyrin is an important finding regarding for the clinical use of this compound.

Example 8

GASTROINTESTINAL ADMINISTRATION

DUODENAL ADMINISTRATION

Mn mesoporphyrin was administered directly into the duodenum in two normal rats under anesthesia. Signal intensity in the liver increased 65% and 20% over baseline at 120 minutes, as compared to a control animal.

GASTRIC ADMINISTRATION

A mixture of Mn mesoporphyrin and mixed micelles (40 mM taurocholate and 40 mM monoolein) at varying concentrations (as shown in FIG. 8) was prepared following the procedure of Example 2, and administered to awake rats via gastric lavage at 4 different concentration of Mn mesoporphyrin and micelles. As shown in FIG. 8, at a concentration of 0.05 mmol Mn mesoporphyrin and 0.26 mmol mixed micelles per kg of rat body weight, normal liver tissue was enhanced 65% over baseline (rats were imaged 4 hours post administration and were awake during the interval). In one rat with a liver metastases, gastric administration of the same formulation (0.05 mmol/kg Mn mesoporphyrin and 0.26 mmol/kg mixed micelles) caused significant increase of the tumor-to-liver contrast as compared to a control animal (single observation, see also FIG. 2).

As can be seen from the foregoing, a liver enhancement effective dose of Mn mesoporphyrin can be administered orally and the enhancement properties of orally administered Mn mesoporphyrin with respect to tumor-to-liver contrast are substantially equivalent to the properties established for intravenous administration.

Example 9

Biodistribution Study in Rats

A biodistribution study in 27 normal rats was completed for 3 doses of Mn mesoporphyrin (0.005, 0.025, and 0.05 mmol/kg, administered i.v.) up to 2 hours post injection, with samples obtained at 10, 30, 60, and 120 min (n=3 rats per dose and time point).

Referring to FIG. 9, Mn-levels in control (sal) animals and rats were determined as described in Example 3, and are shown at 60 min (FIG. 9A) and 120 min (FIG. 9B) following i.v. administration of 5, 25, and 50 umol/kg Mn mesoporphyrin.

Separate in vitro experiments were performed confirming that cholestyramine binds Mn mesoporphyrin, as previously reported (Tishler PV and Winston SH, 1985). Additional prior studies on bioexcretion of lipophilic manganese porphyrins suggest that they undergo biliary excretion and enter an enterohepatic circulation that can be interrupted by the oral administration of cholestyramine thus accelerating the excretion of the compound. (Cegnar, JM, et al, 1988). The stool concentration of a series of rats receiving 0.05 mmol/kg of manganese mesoporphyrin iv, after which stool and urine were collected at 24 hour intervals in metabolic cage containers for 9 days, as shown in FIG. 10. Urine contained no manganese detectable by flame atomic absorption spectrophotometry. Stool concentrations on day 2 revealed a statistically significant (by paired student's t-test) increase (p less than 0.05) in manganese concentration in animals fed 140 mg/kg of cholestyramine compared to an experimental group receiving the manganese porphyrin and no cholestyramine, a group receiving cholestyramine alone, and a control group. The apparent "rebound" in stool manganese concentration in animals receiving manganese mesoporphyrin without the chelating agent indicates that the compound may be excreted in the bile and undergoes enterohepatic circulation. The majority of an i.v. dose is excreted in the feces within 72 hours in normal rats.

The foregoing studies on in vivo biodistribution of Mn mesoporphyrin demonstrate that the compound is preferentially taken up by the normal liver and excreted through the hepatobiliary system. The studies on intravenous or oral toxicity of Mn mesoporphyrin in normal animals and animals with extensive liver disease suggest that Mn mesoporphyrin can be administered safely at an effective dose. Furthermore both imaging and biodistribution data show that the compound is largely cleared from the liver and into the feces within 72 hours. The excretion of Mn mesoporphyrin seems substantially further increased by administration of cholestyramine, an observation which suggests that the compound may undergo enterohepatic circulation and that cholestyramine administration can hasten stool excretion. Studies comparing lymph and plasma manganese content following intestinal administration of the material in mixed micelles show little evidence and significant amounts of the material ever reaches the systemic circulation, suggesting (in combination with FIG. 1) a relatively high first pass uptake by the liver.

Literature Cited

Blatter D, Burnham BL, David PL, Nelson JA: "Mn-Protoporphyrin IX and Mn-Uroporphyrin: tissue selective magnetic resonance contrast agents," (1985) Unpublished manuscript.

Bohdiewicz PJH, Lavallee DK, Fawwaz RA, Newhouse JH, Oluwolfe JH, and Alderson PO: "Mn(III) hematoporphyrin a potential MR contrast agent," (1990) *Invest Radiol* 25:765770.

Brasch RC: "Methods of contrast enhancement for NMR imaging and potential applications: a subject review," (1982) *Radiology* 147:781-788.

Casarett LJ, Doull J: "Evaluation of safety: toxocologic evaluation," *Toxicology: The basic science of poisons*, 2nd ed., Doull J. Klassen CD, Amdur MO, eds. New York: MacMillen 1980; 1-27.

Cegnar JC, Pharris CJ, Shankland EG, Nelson JA: "Adsorption of lipophilic contrast agent with cholestyramine," AUR Annular Meeting New Orleans, LA. Poster Session (1988).

Chen C, Cohen JS, Myers CE, Sohn M: "Paramagnetic metalloporphyrins as potential contrast agents in NMR imaging," (1984) *Febs Lett* 168:70-74.

Fiel RJ, Button TM, Gilani S, et al: "Proton relaxation enhancement by Mn(III)TPPS4 in a model tumor system," (1987) *Mag Res Imag* 5:149-156.

Fiel RJ, Musser DA, Mark EH, Hazurchuk R, and Alletto JJ: "A comparative study of manganese meso-sulfonatophenyl prophyrins: Contrast enhancing Agents for Tumors," (1990) *Mag. Res. Imaging* 8:255-259

Feeney PC and Marks WM: "Computed tomographic arteriography of the liver," (1983) *Radiology* 148:193-197.

Feeney PC and Marks WM: "Hepatic perfusion abnormalities during CT angiogaphy: detection and interpretation," (1986) *Radiology* 159:685-691.

Gouterman M: Electronic spectra: The porphyrins, Academic Press (1978).

Heiken JP, Wevman PJ, Lee JKT, Balfe, DM, et. al: "Detection of Focal Hepatic Masses: Prospective Evaluation with CT, Delayed CE, CT dun'n, Arterial Portogaphy, and MR imagine," (1989) *Radiology* 171:147-51.

Jackson LS, Nelson JA, Case TA, Burnham BF: "Manganese Protoporphyrin LX. A potential intravenous paramagnetic NMR contrast aoent: Preliminary comunication," (1985) *Invest Radiol* 20:226-229.

Lasser EC: *Dynamic Factors in Toentgen Diagnosis* (1967) Baltimore, Williams & Wilkens.

Maines NM: "Zinc-protoporphyrin is a selective inhibitor of heme oxygenase activity in the neonatal rat," (1981) *Biochem et Biophys Acta* 673:339-350.

Majumdar S, Zoghbi SS, and Gore JC: "Parmacokinetics of superparamagnetic Iron-oxide MR contrast anents in the Rat," (1990) *Invest. Radiol.* 25:771-777.

Mirowitz SA, Lee JKT, Gutierrez E Brown JJ, et al: Abstract #161, *SMRM Book of Abstracts*, Vol. 1, Aug, 1990.

Morton KA, Alazraki NP, Datz FL, Taylor AT, Winge, D, Lynch: "RE: Uptake of Cadrriium- 109, a metailothionein-binding radiometal, by tumors in mice as a function of the transformed phenotype," (1988) *Invest Radiol* 23:200-204.

Nelson JA, Satubus AE, and Riegelman S: "Saturation kinetics of iopanoate in the dog," (1975) *Invest Radiol* 10:371-377.

Nelson JA, Cegnar J, Spence ?? Richards TL, Golden RN, Muzi M: "Lipophilic manganese porphyrin crosses blood-brain barrier," (1987). RSNA, Chicago, Ill., Paper #903.

Nelson JA, Sheya P, David PL, Bommer JC: "Kinetic studies of manganese mesoporphyrin," In Runge, Claussen, Felix, and James eds (1986) 74-75.

Nelson JA, Schmiedel U, and Shankland EG: "Metalloporphyrins as tumor-seeking NMI contrast media and as potential selective treatment sensitizers," (1990) *Invest Radiol* 25: S71-S73.

Ogan MD, Revel D, Brasch RC: "Metalloporphyrin contrast enhancement of tumors in Magnetic resonance imaging. A study of human carcinoma, lymphoma, and fibrosarcoma in mice," (1987) *Invest Radiol* 22:822-828.

Patrizio G. Pavone P, De Stefano N, and Passariello R: "GD-BOPTA: Efficacy of a new hepatobiliary contrast agent in case of experimentally induced obstructive jaundice as compared to GD-DTPA," (1990) *SMRM Book of Abstracts,* abstract 23 1.

Patronas NJ, Cohen JS, Knop RH, Dwyer AJ, Colcher D, Lundy J, Momex F, Hambright P, Sohn M, Myers CE: "Metalloporphyrin contrast contrast agents for magnetic resonance imaging of human tumors in mice," *Cancer Treat Rep* 70:391-395 (1987).

Rice, RP: "Lowering Death Rates form Colorectal Cancer: Challenge for the 1990s," (1990) *Radiology* 176: 297-301.

Runge VA, Stewart RG, Glanton JA, et al: "Work in progress: potential oral and intravenous paramagnetic NMR contrast agents," (1983) *Radiol* 147:789-791.

Saini S, Stark DD, Wittenberg J, et al: "A rat model of liver cancer for imaging research," (1987) *Invest Radiol* 22:14914 152.

Schmiedel U, Koelbel G, Hess CF, Klose U, and Kurtz B: "Dynamic sequential MR imaging of focal liver lesions: initial experience in 22 patients at 1.5 T," (1990) *JCAT* 14:600-607.

Sekijima JH, Park HZ, and Lee SP: "A calcium binding protein in hepatic bile," (1990) *Gastroent.* 98 (No. 5, Pan 2) AASLD Abstracts, A630.

Spike JD: "Porphyrins and related compounds as photodynamic sensitizers," (1975) *Ann NY Acad Sci* 244:496.

Stark DD, Wittenberg J, Butch RJ, Ferrucci JT: "Hepatic metastases: randomized, controlled comparison of detection with MR imaging and CT," (1987) *Radiology* 165:399-406.

Stark DD, Weissleder R. Elizondo G. et al: "Superparamagnetic iron oxide: Clinical applications as a contrast agent for MR imaging of the liver," (1988) *Radiology* 168:297-301.

Swistel JA, Bading JR, Raay JH: "Intraarterial Versus Intravenous Adriamycin in the Rabbit Vx-2 Tumor System," *Cancer* 53(6):1397-1404.

Thomson JM, Maruyama Y, Schwartz S, Hahn E: "Effect of chemotherapy and/or irradiation on survival of mice with intracranial glioma," (1971) *Radio* 10 1:187-194.

Tishler PV and Winston SH: "Sorbent therapy of the porphyrias. IV. Adsorption or porphyrins by sorbents in vitro," (1985) *Met and Find Clin Pharmacol* 7:485-491.

Unger E, Tilcock C, Ahkong QF, and Fritz T: "Paramagnetic liposomes as magnetic resonance contrast agents," (1990) *Invest Radiol* 25:S65-S66

Weinstein WM, Onderdonk AB, Bartlett JG et al: "Experimental intraabdominal abscesses in rats: development of an experimental model," (1975) *Infect Immun* 10:1250-1255.

While the invention has been described in connection with certain presently preferred and illustrative embodiments, various modifications and equivalents will be apparent from the foregoing to those of ordinary skill in the art. Any such modifications and equivalents are intended to be within the scope of the appended claims except insofar as precluded by the prior art.

What is claimed is:

1. A method of altering NMR relaxation times in the hepatobiliary magnetic resonance imaging of a human or animal subject, comprising enterically administering to the subject in an amount effective to lower the T1 relaxivity in heptacytes of the subject, a lipophilic contrast enhancing agent having an octanol:water coefficient of at least about 2:1, the lipophilic contrast enhancing agent comprising a chelating ligand and a paramagnetic ion of the transition metal or lanthanide series.

2. The method of claim 1 wherein the chelating ligand is selected from the group consisting of mesoporphyrins, protoporphyrins, deuteroporphyrins, pheophorbides, pyropheophorbides and chlorin-$e_6$.

3. The method of claim 2 wherein the paramagnetic moiety is selected from the group consisting of gadolinium (III), iron (III), manganese (II and III), chromium (III), copper (II), dyprosium (III), terbium (III), holmium (III), erbium (III), and europium (III).

4. The method of claim 1 wherein the contrast enhancing agent is Mn mesoporphyrin.

5. The method of claim 1 wherein the contrast enhancing agent is orally administered to the subject together with an enteric delivery agent.

6. The method of claim 5 wherein the contrast enhancing agent is administered to the subject in the form of a tablet, capsule or pill, and the enteric delivery agent comprises an enteric coating.

7. The method of claim 5 wherein the contrast enhancing agent is administered to the subject in the form of a liquid suspension, and the enteric delivery agent comprises mixed liposomes and micelles.

8. The method of claim 1 wherein the contrast enhancing agent is rectally administered to the subject.

9. The method of claim 8 wherein the enteric delivery system comprises a suppository.

10. The method of claim 1 wherein from about 0.1 to about 50 mg of the contrast enhancing agent per kg of body weight is administered to the subject.

11. The method of claim 7 wherein from about 1 to about 10 mg of the contrast enhancing agent per kg of body weight is administered to the subject.

12. The method of treating a subject comprising enterally administering to the subject a lipophilic porphyrin agent having an octanol:water coefficient of at least about 2:1, the porphyrin agent comprising a chelating ligand and a paramagnetic ion of the transition metal or lanthanide series, together with an enteric delivery agent.

13. The method of claim 12 wherein the lipophilic porphyrin agent is administered to the subject in the form of a liquid suspension, and the enteric delivery agent comprises mixed liposomes or micelles.

14. The method of claim 13 wherein the enteric delivery agent comprises micelles formed by taurocholic acid and monoolein.

* * * * *

UNITED STATES PATENT AND TRADEMARK OFFICE
CERTIFICATE OF CORRECTION

PATENT NO. : 5,169,944
DATED : December 8, 1992
INVENTOR(S) : J.A. Nelson et al.

Page 1 of 3

It is certified that error appears in the above-identified patent and that said Letters Patent is hereby corrected as shown below:

| COLUMN | LINE | |
|---|---|---|
| | | On title page, item |
| [56] | 1st Ref. | "4,393,071 7/1983 Fujii et al." should read --4,393,071 7/1983 Fjuii et al.-- |
| [56] | 2nd Publ. | "8:255-259, 1990" should read --8:225-259, 1990-- |
| [56] | 8th Publ. | after "media" insert --and-- |
| [57] | 8 | "pyrophenophoribide" should read --pyropheophoribide-- |
| 1 | 22 | "unncessary" should read --unnecessary-- |
| 1 | 44 | "Hepatorophic" should read --Hepatotrophic-- |
| 1 | 64 | "Schmiedel" should read --Schmiedl-- |
| 3 | 32 | "prophyrin" should read --porphyrin-- |
| 3 | 35 | "usign" should read --using-- |
| 4 | 8 | "heptabiliary" should read --hepatobiliary-- |
| 5 | 14 | "(sal" should read --(sal)-- |
| 5 | 27 | "heptabiliary" should read --hepatobiliary-- |
| 5 | 67 | "magnetron" should read --magneton-- |
| 7 | 1 | "diluent" should read --diluents-- |
| 7 | 2 | "lubricanting" should read --lubricating-- |
| 7 | 15 | "suspension" should read --suspensions-- |
| 7 | 17 | "Beside" should read --Besides-- |
| 8 | 39 | "550 mm" should read --550 nm-- |
| 9 | 34 | "shown" should read --show-- |
| 9 | 50 | after "was" delete "in" |
| 9 | 60-61 | delete "Monoolein/Taurocholic acid Solution (micelle Solu-tion)" |
| 10 | 63 | "usign" should read --using-- |

UNITED STATES PATENT AND TRADEMARK OFFICE
CERTIFICATE OF CORRECTION

PATENT NO. : 5,169,944

DATED : December 8, 1992

INVENTOR(S) : J.A. Nelson et al.

Page 2 of 3

It is certified that error appears in the above-identified patent and that said Letters Patent is hereby corrected as shown below:

| COLUMN | LINE | |
|---|---|---|
| 11 | 7 | "grown" should read --growth-- |
| 11 | 23 | "n" should read --an-- |
| 12 | 24 | "0.054 M" should read --0.04 M-- |
| 12 | 29 | "at" should read --as-- |
| 12 | 53 | "Vx-2tumor" should read --Vx-2 tumor-- |
| 13 | 17 | "3" should read --3 ml-- |
| 14 | 3 | "7.34" should read --7.45-- |
| 14 | 12 | "monolein" should read --monoolein-- |
| 14 | 51 | "MHz" should read --Mhz-- |
| 14 | 54 | after "that" insert --of-- |
| 14 | 55 | "pin" should read --spin-- |
| 15 | 29 | "sprague" should read --Sprague-- |
| 16 | 14 | "rats+" should read --rats'-- |
| 16 | 17 | "resonantor" should read --resonator-- |
| 17 | 2 | delete "the" (second occurrence) |
| 17 | 14 | "Fischer" should read --Fisher-- |
| 17 | 48 | "adenocarbinoma" should read --adenocarcinoma-- |
| 19 | 29 | "2revealed" should read --2 revealed-- |
| 20 | 2 | "JH" (2nd Occurrence) should read --JF-- |
| 20 | 22 | "Hazurchuk" should read --Mazurchuk-- |
| 20 | 27 | "Feeney" should read --Freeney-- |
| 20 | 30 | "Feeney" should read --Freeny-- |
| 20 | 44 | "comunication" should read --communication-- |
| 20 | 45 | "Toentgen" should read --Roentgen-- |
| 20 | 50-51 | "Parmacokinet-ics" should read --Pharmacokinetics-- |

UNITED STATES PATENT AND TRADEMARK OFFICE
CERTIFICATE OF CORRECTION

PATENT NO. : 5,169,944
DATED : December 8, 1992
INVENTOR(S) : J.A. Nelson et al.

It is certified that error appears in the above-identified patent and that said Letters Patent is hereby corrected as shown below:

| COLUMN | LINE | |
|---|---|---|
| 20 | 62 | "Satubus" should read --Staubus-- |
| 21 | 1 | "David" should read --Davis-- |
| 21 | 4 | "Schmiedel" should read --Schmiedl-- |
| 21 | 26 | "Glanton" should read --Clanton-- |
| 21 | 32 | "22:14914 152" should read --22:149-152-- |
| 21 | 33 | "Schmiedel" should read --Schmiedl-- |
| 21 | 56 | "Radio" should read --Radiol-- |
| 21 | 59 | "or" should read --of-- |
| 22 | 15 | "heptacytes" should read --hepatocytes-- |
| 22 | 27 | "dyprosium" should read --dysprosium-- |

Signed and Sealed this

Sixteenth Day of November, 1993

Attest:

BRUCE LEHMAN

*Attesting Officer*  *Commissioner of Patents and Trademarks*